US006348353B1

(12) United States Patent
Harrington et al.

(10) Patent No.: US 6,348,353 B1
(45) Date of Patent: *Feb. 19, 2002

(54) ARTIFICIAL MAMMALIAN CHROMOSOME

(75) Inventors: John J. Harrington, Willoughby Hills, OH (US); Gil B. Van Bokkelen, Los Altos, CA (US); Huntington F. Willard, Shaker Hts., OH (US)

(73) Assignee: Case Western Reserve University, Cleveland, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/643,554

(22) Filed: May 6, 1996

Related U.S. Application Data

(63) Continuation-in-part of application No. 08/487,989, filed on Jun. 7, 1995, now Pat. No. 5,695,967.

(51) Int. Cl.⁷ .......................... C12N 15/85; C12N 15/79

(52) U.S. Cl. .................... 435/455; 435/320.1; 536/23.1

(58) Field of Search ........................ 435/320.1, 172.3, 435/455; 514/44; 536/23.1

(56) References Cited

U.S. PATENT DOCUMENTS

| | | | |
|---|---|---|---|
| 4,889,806 A | * 12/1989 | Olsen et al. | 435/172.3 |
| 5,049,504 A | 9/1991 | Maugh et al. | 435/252.33 |
| 5,149,657 A | 9/1992 | Maugh et al. | 435/320.1 |
| 5,202,236 A | 4/1993 | Maugh et al. | 435/69.1 |
| 5,202,256 A | 4/1993 | Maugh et al. | 435/252.3 |
| 5,242,808 A | 9/1993 | Maugh et al. | 435/69.1 |
| 5,288,625 A | 2/1994 | Hadlaczky | 435/172.2 |
| 5,695,967 A | 12/1997 | Van Bokkelen et al. | 435/91.1 |
| 5,869,294 A | 2/1999 | Harrington et al. | 435/91.1 |

FOREIGN PATENT DOCUMENTS

| | | |
|---|---|---|
| EP | 0 532 050 | 3/1993 |
| FR | 2 593 827 | 8/1987 |
| WO | WO 91/07496 | 5/1991 |
| WO | WO 92/07080 | 4/1992 |
| WO | WO 95/32297 | 11/1995 |
| WO | WO 96/40965 A1 | 12/1996 |

OTHER PUBLICATIONS

DePamphilis, Melvin L., "Replication origins in Metazoan Chromosomes: Fact or Fiction," *BioEssays* 21:5–16, (1999), John Wiley & Sons, Inc.

Shaw, David, "Artificial Chromosomes: A Blueprint for the Future," *Australian National University*, Biologist (2000) 47(1), Institute fo Biology.

Henning, Karla A., "Human Artificial Chromosomes Generated by Modification of a Yeast Artificial Chromosomes Containing Both Human Alpha Satellite and Single–Copy DNA Sequences," *Proc. Natl. Acad. Sci. USA* vol. 96, pp. 592–597, (1999), National Academy fo Sciences of the USA.

Grimes, Brenda et al., "Engineering Mammalian Chromosomes," *Human Molecular Genetics*, 1998, vol. 7, No. 10 Review, pp. 1635–1650 (1998), Oxford University Press.

Krysa, Patrick J. et al., "Isolation of Human Sequences That Replicate Autonomously in Human Cells," *Molecular and Cellular Biology*, pp. 1026–1033 (1989), American Society for Micrbiology.

Heinzel, Scott S. et al., "Autonomous DNA Replication in Human Cell Is Affected by the Size and the Source of the DNA," *Molecular and Cellular Biology*, pp. 2263–2272 (1991), American Society for Microbiology.

Aladjem, Mirit I. et al., "Genetic Dissection of a Mammalian Replicator in the Human β–Globin Locus," *Science* vol. 281, (1998), Association for the Advancement of Science.

Nonet et al., Introduction of YACs containing a putative mammalian replication origin inot mammalian cells can generate structures that replicate autonomously, Somat. Cell Mol. Genet. 19 (2): 171–192, 1993.*

DePamphilis, M.L., "Eukaryotic DNA replication: anatomy of an origin", Annu. Rev. Biochem. 62: 29–63, 1993.*

Brown, W.R.A., "Mammalian artificial chromosomes," *Curr. Opin. Genet. Devel.* 2:479–486 (Jun. 1992).

Brown, W., et al., "Mammalian artificial chromosomes," *Curr. Opin. Genet. Devel.* 3:281–287 (Jun. 1996).

Monaco, A.P., and Larin, Z., "YACs, BACs, PACs and MACs: artificial chromosomes as research tools," *Trends in Biotechnol.* 12:280–286 (Jul. 1994).

Ikeno, M., et al., "Construction of YAC–based mammalian artificial chromosomes," *Nature Biotechnol.* 16:431–439 (May 1998).

Schindelhauer, D., and Cooke, H.J., "Efficient combination of large DNA in vitro: in gel site specific recombination (IGSSR) of PAC fragments containing α satellite DNA and the human HPRT gene locus," *Nucl. Acids Res.* 25:2241–2243 (Jun. 1997).

Willard, H.F., "Human artificial chromosomes coming into focus," *Nature Biotechnol.* 16:415–416 (May 1998).

(List continued on next page.)

*Primary Examiner*—Scott D. Priebe
(74) *Attorney, Agent, or Firm*—Sterne, Kessler, Goldstein & Fox P.L.L.C.

(57) ABSTRACT

The invention relates to the field of gene therapy, gene expression, and vectors for these uses. In particular, the invention relates to the development and use of an artificial or synthetic chromosome for gene expression and gene therapy in mammals, and especially humans. The invention allows the controlled construction of stable synthetic or artificial chromosomes constructed from isolated segments of purified DNA. Functional minimal segments preferably include centromeric DNA, telomeric DNA, and genomic DNA. The artificial chromosome performs the essential chromosomal functions of naturally-occurring chromosomes so as to permit the chromosome to function as an effective vector for gene therapy.

4 Claims, 10 Drawing Sheets

(5 of 10 Drawing Sheet(s) Filed in Color)

OTHER PUBLICATIONS

Derwent WPI Accession No. 87–265912/198738, English–language abstract for France Patent Publication No. FR 2593827 from Dialog file 351.

Harrington, J.J. et al., "Formation of de novo centromeres and construction of first–generation human artificial microchromosomes," *Nature Genetics* 15:345–355 (Apr. 1997).

Weiss, R., "Artificial Human Chromosomes that Replicate Developed in Lab. Scientists Aim to Ferry Curative Genes to Cells," *Washington Post*, p. A01 (Apr. 1, 1997).

DePamphilis; Eukaryotic DNA Replication: Anatomy of an Origin, 1993, Annu. Rev. Biochem, 62: 29–63.*

Willard, "Chromosome manipulation: A systematic approach toward understanding human chromosome structure and function", Proc. Natl. Acad. Sci. USA 93: 6847–6850, Jul. 1996.*

Huxley et al., "Ordering up big MACs", Bio/Technology 12: 586–590, Jun. 1994.*

Orkin et al. , "Report and Recommendations of the panel to assess the NIH investment is research on gene therapy", issued by the National Institutes of Health, Dec. 1995.*

Brown, K.E. et al., "Dissecting the centromere of the human Y chromosome with cloned telomeric DNA," *Hum. Mol. Genet.* 3(8):1227–1237 (Aug. 1994).

Brutlag, D. et al., "Synthesis of Hybrid Bacterial Plasmids Containing Highly Repeated Satellite DNA," *Cell* 10(3):509–519 (1977).

Farr, C.et al., "Functional reintroduction of human telomeres into mammalian cells," *Proc. Natl. Acad. Sci. USA* 88:7006–7010 (Aug. 1991).

Ge, Y. et al., "Sequence, Higher Order Repeat Structure, and Long–Range Organization of Alpha Satellite DNA Specific to Human Chromosome 8," *Genomics* 13:585–593 (1992).

Haaf, T. et al., "Integration of Human α–Satellite DNA into Simian Chromosomes: Centromere Protein Binding and Disruption of Normal Chromosome Segregation," *Cell* 70(4):681–696 (1992).

Hadlaczky, G. et al., "Centromere formation in mouse cells cotransformed with human DNA and a dormant marker gene," *Proc. Natl. Acad. Sci. USA* 88:8106–8110 (1991).

Hartley, J.L. and Gregori, T.J.,"Cloning multiple copies of a DNA segment," *Gene* 13:347–353 (1981).

Hofer, B., "Construction and stability of a sixfold repeated artificial gene," *Eur. J. Biochem.* 167:307–313 (1987).

Hosoda, F. et al., "An F factor based cloning system for large DNA fragments," *Nucleic Acids Res.* 18(13):3863–3869 (1990).

Huxley, C., "Mammalian artificial chromosomes: a new tool for gene therapy," *Gene Therapy* 1:7–12 (Jan. 1994).

Hwang, E.S. and Scocca, J.J., "A Method of Cloning Multiple Direct Repeats of a DNA Segment," *BioTechniques* 14(5):766–767 (1993).

Kellogg, D.R. et al., "The Centrosome and Cellular Organization," *Annu. Rev. Biochem.* 63:639–674 (Jul. 1994).

Kovacic, R.T. et al., "Protection of megabase DNA from shearing," *Nucleic Acids Res.* 23(19):3999–4000 (Oct. 1995).

Larin, Z. et al., "De novo formation of several features of a centromere following introduction of a Y alphoid YAC into mammalian cells," *Hum. Mol. Genet.* 3(5):689–695 (May 1994).

Leonhardt, H. and Alonso, J.C., "Parameters affecting plasmid stability in *Bacillus subtilis*," *Gene* 103:107–111 (1991).

Neil, D.L. et al., "Structural instability of human tandemly repeated DNA sequences cloned in yeast artificial chromosome vectors," *Nucleic Acids Res.* 18(6):1421–1428 (1990).

Oakey, R. and Tyler–Smith, C., "Y Chromosome DNA Haplotyping Suggests That Most European and Asian Men Are Descended from One of Two Males," *Genomics* 7:325–330 (1990).

O'Connor, M. et al., "Construction of Large DNA Segments in *Escherichia coli*," *Science* 244:1307–1312 (1989).

Pan, A. et al., "Construction of multiple copy of α–domain gene fragment of human liver metallothionein $I_A$ in tandem arrays and its expression in transgenic tobacco plants," *Protein Engineering* 6(7):755–762 (1993).

Rosenfeld, P.J. and Kelly, T.J., "Purification of Nuclear Factor I by DNA Recognition Site Affinity Chromotography," *J. Biol. Chem.* 261(3):1398–1408 (1986).

Sambrook, J. et al., in: *Molecular Cloning, A Laboratory Manual*, 2nd ed., Cold Spring Harbor Press (1989).

Schalkwyk, L.C. et al., "Techniques in mammalian genome mapping," *Curr. Opin. Biotech.* 6:37–43 (Jan. 1995).

Shizuya, H. et al., "Cloning and stable maintenance of 300–kilobase–pair fragments of human DNA in *Escherichia coli* using an F–factor–based vector," *Proc. Natl. Acad. Sci. USA* 89:8794–8797 (1992).

Sinden, R.R. et al., "On the Deletion of Inverted Repeated DNA in *Escherichia coli*: Effects of Length, Thermal Stability, and Cruciform Formation in Vivo," *Genetics* 129:991–1005 (1991).

Taylor, S.S. et al., "Addition of functional human telomeres to YACs," *Human Molecular Genetics* 3(8):1383–1386 (Aug. 1994).

Taylor, W.H. and Hagerman, P.J., "A general method for cloning DNA fragments in multiple copies," *Gene* 53:139–144 (1987).

Tyler–Smith, C. and Willard, H.F., "Mammalian chromosome structure," *Curr. Opin. Genet. Develop.* 3:390–397 (1993).

Waye, J.S. and Willard, H.F., "Nucleotide sequence heterogeneity of alpha satellite repetitive DNA: a survey of alphoid sequences from different human chromosomes," *Nucleic Acids Res.* 15(18):7549–7569 (1987).

Waye, J.S. and Willard, H.F., "Structure, Organization, and Sequence of Alpha Satellite DNA from Human Chromosome 17: Evidence for Evolution by Unequal Crossing–Over and an Ancestral Pentamer Repeat Shared with the Human X Chromosome," *Molec. Cell. Biol.* 6(9):3156–3165 (1986).

Wevrick, R. and Willard, H.F., "Long–range organization of tandem arrays of α satellite DNA at the centromeres of human chromosomes: High–frequency array–length polymorphism and meiotic stability," *Proc. Natl. Acad. Sci. USA* 86(23) 9394–9398 (1989).

Willard, H.F., "Centromeres of mammalian chromosomes," *TIG* 6(12):410–415 (1990).

Willard, H.F. and Davies, K.E., "Mammalian genetics," *Curr. Opin. Genet. Develop.* 3:387–389 (1993).

Willard, H.F. et al., "Human Centromere Structure: Organization and Potential Role of Alpha Satellite DNA," *In: Mechanisms of Chromosome Distribution and Aneuploidy*, Resnick et al., eds., Alan R. Liss, Inc., pp. 9–18 (1989).

* cited by examiner

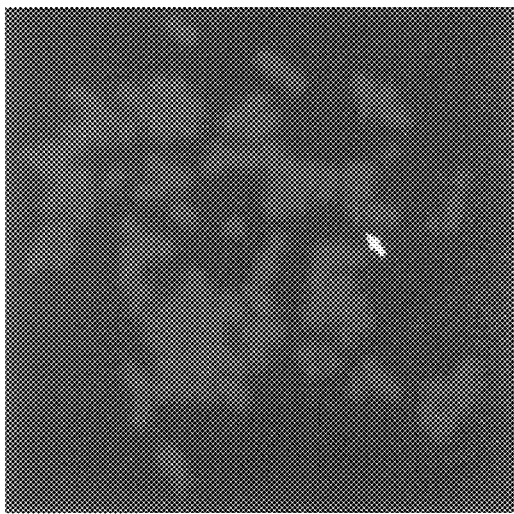
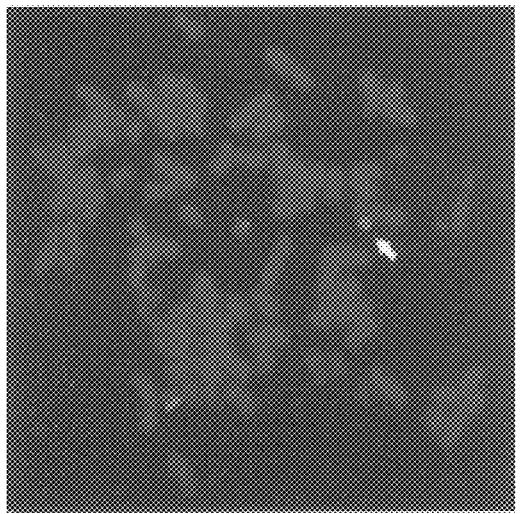
FIG.3A   FIG.3B
FIG.3C   FIG.3D

| Clone | Transfected DNA | Estimated Amount of Synthetic Alpha Satellite DNA |
|---|---|---|
| HT1080 | ∅ | ∅ |
| 22-6 | synthetic Y alpha satellite | 450 kb |
| 22-7 | synthetic Y alpha satellite | 1 mb |
| 22-11 | synthetic Y alpha satellite | 400 kb |
| 22-13 | synthetic Y alpha satellite | 2 mb |
| 23-1 | synthetic 17 alpha satellite | ∅ |

Fig 6B

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 17 base pairs
      (B) TYPE: nucleic acid
      (C) STRANDEDNESS: both
      (D) TOPOLOGY: both (ii) MOLECULE TYPE: DNA (genomic)

(xi) SEQUENCE DESCRIPTION: SEQ ID NO: 1:

ATTCGTTGGA AACGGGA       17

(2) INFORMATION FOR SEQ ID NO: 2:

(i) SEQUENCE CHARACTERISTICS:
      (A) LENGTH: 39 base pairs
      (B) TYPE: nucleic acid
      (C) STRANDEDNESS: both
      (D) TOPOLOGY: linear (ii) MOLECULE TYPE: cDNA (xi) SEQUENCE DESCRIPTION: SEQ ID NO: 2:

GGGTTAGGGT TAGGGTTAGG GTTAGGGTTA GGGTTAGGG       39

(2) INFORMATION FOR SEQ ID NO: 3:

(i) SEQUENCE CHARACTERISTICS:
      (A) LENGTH: 39 base pairs
      (B) TYPE: nucleic acid
      (C) STRANDEDNESS: both
      (D) TOPOLOGY: linear (ii) MOLECULE TYPE: cDNA (xi) SEQUENCE DESCRIPTION: SEQ ID NO: 3:

CCCTAACCCT AACCCTAACC CTAACCCTAA CCCTAACCC       39

ARTIFICIAL MAMMALIAN CHROMOSOME

CROSS REFERENCE TO RELATED APPLICATION

This application is a continuation-in-part application of U.S. application Ser. No. 08/487,989, filed Jun. 7, 1995, now U.S. Pat. No. 5,695,967.

FIELD OF THE INVENTION

The invention relates to the field of gene expression and gene therapy, and to novel vectors for these uses. In particular, the invention relates to the development and use of an artificial or synthetic chromosome as a vector for gene expression and gene therapy, especially in humans. The invention enables the controlled construction of stable synthetic or artificial chromosomes from isolated purified DNA. With this DNA, a functional chromosome is formed in a cell and maintained as an extrachromosomal element. The artificial chromosome performs the essential chromosomal functions of naturally-occurring chromosomes so as to permit the chromosome to function as an effective vector for gene therapy when therapeutic DNA is included in the chromosome.

BACKGROUND OF THE INVENTION

The genetic manipulation of cells aimed at correcting inherited or acquired disease is referred to as gene therapy. Until now, most clinical studies in this field have focused on the use of viral gene therapy vectors. Based on the results of these studies, it is becoming clear that current viral gene therapy vectors have severe clinical limitations. These include immunogenicity, cytopathicity, inconsistent gene expression, and limitations on the size of the therapeutic gene. For these reasons, much attention has been recently focused on the use of non-viral gene therapy vectors.

In particular, synthetic mammalian chromosomes would be useful vectors for facilitating a variety of genetic manipulations to living cells. The advantages of synthetic mammalian chromosomes include high mitotic stability, consistent and regulated gene expression, high cloning capacity, and non-immunogenicity.

Artificial chromosomes were first constructed in *S. cerevisiae* in 1983 (Murray et al., *Nature* 305:189–193 (1983), and in *S. pombe* in 1989 (Hahnenberger et al., *Proc. Natl. Acad. Sci. USA* 86:577–581 (1989). For many reasons, however, it has not been obvious whether similar vectors could be made in mammalian cells.

First, multicellular organisms (and thus the progenitors of mammalian cells) diverged from yeast over 1 billion years ago. Although there are similarities among living organisms, in general, the similarities among two organisms are inversely related to the extent of their evolutionary divergence. Clearly, yeast, a unicellular organism, is radically different biologically from a complex multicellular vertebrate.

Second, yeast chromosomes are several orders of magnitude smaller than mammalian chromosomes. In *S. cerevisiae* and *S. pombe*, the chromosomes are 0.2 to 2 megabases and 3.5–5.5 megabases in length, respectively. In contrast, mammalian chromosomes range in size from approximately 50 megabases to 250 megabases. Since there is a significant difference in size, it is not clear, a priori, whether constructs comparable to yeast artificial chromosomes can be constructed and transfected into mammalian cells.

Third, yeast chromosomes are less condensed than mammalian chromosomes. This implies that mammalian chromosomes rely on more complex chromatin interactions in order to achieve this higher level of structure. The complex structure (both DNA structure and higher order chromatin structure) of mammalian chromosomes calls into question whether artificial chromosomes can be created in mammalian cells.

Fourth, yeast centromeres are far less complex than mammalian centromeres. In *S. cerevisiae*, for example, the centromere is made up of a 125 bp sequence. In *S. pombe*, the centromere consists of approximately 2 to 3 copies of a 14 kb sequence element and an inverted repeat separated by a core region (~7 kb). In contrast, human centromeres are made up of several hundred kilobases to several megabases of highly repetitive alpha satellite DNA. Furthermore, in mammalian centromeres, there is no evidence for a central core region or inverted repeats such as those found in *S. pombe*. Thus, unlike yeast centromeres, mammalian centromeres are extremely large and repetitive.

Fifth, yeast centromeres have far fewer spindle attachments than mammalian centromeres (Bloom, *Cell* 73:621–624 (1993)). *S. cerevisiae*, for example, has a single microtubule attached to the centromere. In *S. Pombe*, there are 2–4 microtubules attached per centromere. In humans, on the other hand, there are several dozen microtubules attached to the centromere of each chromosome (Bloom, *Cell* 73:621–624 (1993)). This further illustrates the complexity of mammalian centromeres compared to yeast centromeres.

Together, these differences are significant, and do not suggest that a result in yeast can be reasonably expected to be transferable to mammals.

Normal mammalian chromosomes are comprised of a continuous linear strand of DNA ranging in size from approximately 50 to 250 megabases. In order for these genetic units to be faithfully replicated and segregated at each cell division, it is believed that they must contain at least three types of functional elements: telomeres, origins of replication, and centromeres.

Telomeres in mammals are composed of the repeating sequence $(TTAGGG)_n$ and are thought to be necessary for replication and stabilization of the chromosome ends. Origins of replication are necessary for the efficient and controlled replication of the chromosome DNA during S phase of the cell cycle. Although mammalian origins of replication have not been well-characterized at the sequence level, it is believed that they are relatively abundant in mammalian DNA. Finally, centromeres are necessary for the segregation of individual chromatids to the two daughter cells during mitosis to ensure that each daughter cell receives one, and only one, copy of each chromosome. Like origins of replication, centromeres have not been defined at the sequence level. Alpha satellite DNA may be an important centromeric component (Haaf et al., *Cell* 70:681–696 (1992); Larin et al., *Hum. Mol. Genet.* 3:689–695 (1994); Willard, *Trends in Genet.* 6:410–415 (1990)). But there are cases of mitotically stable abnormal chromosome derivatives that apparently lack alpha satellite DNA (Callen et al., *Am. J. Med. Genet.* 43:709–715 (1992); Crolla et al.,*J. Med. Genet.* 29:699–703 (1992); Voullaire et al., *Am. J. Hum. Genet.* 52:1153–1163 (1993); Blennow et al., *Am. J. Hum. Genet.* 54:877–853 (1994); Ohashi et al., *Am. J. Hum. Genet.* 55:1202–1208 (1994)). Thus, at this time, the composition of the mammalian centromere remains poorly understood.

While others have claimed to have produced "artificial" chromosomes in mammalian cells, no one has ever produced an artificial chromosome that contains only exogenous DNA. In each of these previous cases, the investigators either modified an existing chromosome to make it smaller (the "pare-down" approach) or they integrated exogenous DNA into an existing chromosome which then broke to produce a chromosome fragment containing endogenous sequences from the preexisting chromosome (the "fragmentation" approach). In the present invention, exogenous DNA sequences are introduced into human cells and form stable synthetic chromosomes without integration into endogenous chromosomes.

Among the pare-down approaches, three specific strategies have been used: (1) telomere directed truncation via illegitimate recombination (Barnett, M. A. et al., *Nucleic Acids Res.* 21:27–36 (1993); Farr, C. J. et al., *EMBO J.* 14:5444–54 (1995)) (2) alpha satellite targeted telomere insertion/truncation via homologous recombination (Brown, K. E. et al., *Hum Mol. Genet.* 3:1227–37 (1994)) (3) formation/breakage of dicentric chromosomes (Hadlaczlky, G., Mammalian Artificial Chromosomes, U.S. Pat. No. 5,288,625 (1994)).

Barnett et al. (*Nucleic Acids Res.* 21:27–36 (1993)), Farr et al. (*EMBO J.* 14:5444–54 (1995)), and Brown et al. (*Hum Mol. Genet.* 3:1227–37 (1994)) describe methods for fragmenting endogenous chromosomes by transfecting telomeric DNA and a selectable marker into mammalian cells. In each case, a truncated chromosome was created that was smaller than the original chromosome. The resulting truncated chromosomes contained large amounts of endogenous chromosome sequence, including the endogenous centromere. Thus, these chromosomes were not formed de novo.

Hadlaczky (Mammalian Artificial Chromosomes, U.S. Pat. No. 5,288,625 (1994)) describes a cell-line that can be use to propagate a chromosome that was formed as a result of a dicentric chromosome breakage event. All of the sequences, with the exception of a selectable marker were derived from the original, fully functional dicentric chromosome. Thus, these so called "artificial" chromosomes were not created de novo.

Among the "fragmentation" approaches, Haaf et al. (*Cell* 70:681–696 (1992)) and Praznovszky et al. (*Proc. Natl. Acad Sci. USA* 88:11042–11046 (1991)) describe methods for producing chromosome fragments by integrating transfected DNA into endogenous chromosomes. Following transfection, the integrated DNA sequences become amplified (increase in copy number), and in some clones, a portion of the endogenous chromosome breaks off to produce a fragment that exists extrachromosomally. In both references, integrated transfected DNA can be found extensively on the endogenous chromosome and the extrachromosomal fragment.

In the experiments by Haaf et al. (*Cell* 70:681–696 (1992)), human alpha satellite DNA and the neomycin resistance gene were co-transfected into African Green Monkey cells. No other exogenous DNA was included in any of the transfections. In every transfection clone, DNA was found to be integrated into the endogenous chromosomes. In one clone, which was also found to contain an extrachromosomal fragment, the transfected alpha satellite DNA had amplified extensively following integration. The authors conclude, based on Southern blot and Fluorescence In-Situ Hybridization, that African Green Monkey sequences co-amplified with the transfected DNA and were interspersed among the alpha satellite DNA. In further characterization of the chromosomes that contained amplified alpha satellite, it was found that "the number, size, and chromosomal location (telomeric, interstitial, or centromeric) of the transfected chromosome regions varied from cell to cell within the population of line 3–31 cells, suggesting instability of the transfected sequences." Finally, analysis of the mitotic behavior of the chromosomes containing amplified alpha satellite DNA revealed a high incidence of anaphase bridges, suggesting that the chromosomes were dicentric (or multicentric). Thus, the high degree of observed structural instability in conjunction with the high incidence of anaphase bridge structures is consistent with the idea that the chromosome fragment resulted from an integration/amplification/breakage event. Finally, it is also worth noting that in clones that contained integrated, unamplified alpha satellite DNA, no extrachromosomal fragments were observed, further suggesting that amplification is important for the chromosome fragmentation process in this method.

Praznovszky et al. (*Proc. Natl. Acad Sci. USA* 88:11042–11046 (1991)) produced chromosome fragments by integrating a piece of non-centromeric human DNA (later shown to map to human chromosome 9 qter by McGill et al. (*Hum. Mol. Genet.* 1:749–751 (1992)) and Cooper et al. (*Hum. Mol. Genet.* 1:753–754 (1992)) into an endogenous chromosome. Like the Haaf experiment, the integrated transfected DNA amplified extensively, and was found to be interspersed with mouse genomic sequences. The authors suggest that the integration/amplification of the transfected DNA resulted in the formation of a dicentric chromosome that then subsequently broke to produce chromosome fragments. Analysis of the chromosome fragments shows unambiguously that the chromosome fragments were derived from the mouse chromosome containing the integrated amplified DNA.

There are a number of important similarities between the experiments by Haaf et. al. and Praznovszky et. al. First, both show that the transfected DNA integrated into endogenous chromosomes. Second, both show that following integration, the transfected DNA amplified extensively. Third, endogenous DNA (untransfected chromosomal sequences from the recipient cell) was found to be interspersed throughout the amplified sequences. Fourth, the endogenous chromosomes containing the amplified transfected sequences stained with CREST antisera. Fifth, the endogenous chromosomes containing the amplified transfected sequences behaved similarly to dicentric chromosomes during mitosis. Finally, the endogenous chromosomes containing the amplified transfected sequences displayed structural instability. Thus, the large number of important similarities and the demonstrated chromosomal fragmentation by Praznovszky et. al. indicate a chromosome integration/amplification/breakage mechanism in both of these experiments.

Further evidence that transfection and integration of alpha satellite DNA into mammalian chromosomes is not sufficient to create extrachromosomal fragments in the absence of amplification was obtained by Larin et. al. (*Hum. Mol. Genet.* 3:689–95 (1994)). In these experiments, alpha satellite DNA linked to a selectable marker was transfected into human cells. In every drug-resistant clone, the alpha satellite DNA was integrated into an endogenous chromosome. While these integrations formed centromere-like structures (i.e. primary constrictions, CREST antisera staining, and lagging chromosomes during anaphase), no extrachromosomal fragments were observed in any clone. Since these experiments failed to provide clones with chromosomes containing the transfected alpha satellite DNA and not an endogenous centromere, there is no reliable method to determine whether the centromere-like structures that formed are capable of facilitating chromosome segregation.

Since each of the "pared-down" chromosomes was created from a pre-existing chromosome and since each of the "fragmentation" chromosomes was created by integrating DNA into pre-existing chromosomes, these references do not provide guidance about how to create chromosomes de novo from transfected naked DNA.

Furthermore, these chromosomes and the approaches used to make them have severe limitations as gene therapy vectors for several reasons. First, the methods used to make them can only be used to create the chromosomes in cell culture. Since the breakage events are either extremely rare and/or produce chromosomes with unpredictable structure, these methods are not compatible with direct use in patients' cells. Additionally, the instability of the amplified sequences in the fragmentation approach is inconsistent with use in patients due to the risks of genomic rearrangements that, in turn, may lead to cellular transformation and cancer.

It would be highly desirable, therefore, if there were a prefabricated chromosome vector with defined structure that could be introduced directly into patient's cells, especially a vector that did not depend upon integration into endogenous chromosomes or subsequent amplification, and where the structure of the construct in the cell is substantially identical to its structure prior to transfection.

Second, pared-down chromosomes and chromosome fragments are composed of undefined endogenous sequences and provide no guidance for identifying sequences that are functionally important.

It would be highly desirable, therefore, to provide vectors composed of defined sequences and the methods to produce these defined synthetic chromosomes that allow other functionally important sequences to be rapidly identified.

Third, the chromosomes produced by the pare-down and fragmentation approaches can not be substantially purified using currently available techniques. Thus, it is difficult to deliver these pared-down chromosomes to mammalian cells without delivering other mammalian chromosomes.

It would be highly desirable, therefore, to provide substantially purified genetically engineered DNA that can be introduced into a cell and form a functional chromosome.

Fourth, since these pared-down chromosomes and chromosome fragments have never been isolated as naked DNA and reintroduced into a cell, up to the present, it was never clear whether any exogenous DNA could be introduced into a cell to produce a functional chromosome de novo (without integrating into the host chromosomes first).

It would be highly desirable, therefore, to provide artificial mammalian chromosomes that are created de novo by introducing purified DNA into a mammalian cell.

Finally, it is very difficult to add new DNA sequences (e.g. therapeutic genes) to the pared-down chromosomes and chromosome fragments.

It would be highly desirable, therefore, to provide vectors created in vitro, where placing new DNA sequences onto the vectors is straight-forward and efficient.

Sun et. al. (*Nature Genetics* 8:3341 (1994)) describe a viral-based vector system designed for use in human cells. The vector is described as a "human artificial episomal chromosome." However, the vector relies on the presence of EBNA-1, a toxic and immunogenic viral protein. Further, the vector relies on a viral origin of replication and not on a natural mammalian chromosomal replication origin.

Further, the "chromosome" does not contain functional centromeric or telomeric DNA, and does not form a functional kinetochore during mitosis. As a result, such a vector does not segregate in a controlled manner. Finally, the vector is present in the cell at an elevated copy number that ranges from 50 to 100 copies per cell, unlike endogenous chromosomes. Based on these criteria for defining mammalian chromosomes, this vector cannot be properly designated a "human artificial chromosome" because it has different properties and functions by unrelated mechanisms.

Thus, there is still a clear need for a wholly synthetic or artificial chromosome made from DNA that can be manipulated in vitro and, upon transfection into cells, will adopt a functional chromosome structure and will direct gene expression in a controlled manner.

In contrast to the cited art, several embodiments of the current invention describe a prefabricated chromosome vector with defined structure and composition that can be introduced directly into patients' cells. Since the vector described in this invention does not depend upon integration into endogenous chromosomes or subsequent amplification, the structure of the construct in the cell is substantially identical to its structure prior to transfection.

In contrast to the cited art, the vectors described in this present invention are composed of defined sequences. Furthermore, the methods used to produce these synthetic chromosomes allow other functionally important sequences to be rapidly identified.

In contrast to the cited art, with the present invention, the inventors demonstrate for the first time that artificial mammalian chromosomes can be created de novo by introducing purified DNA into a mammalian cell.

In contrast to the cited art, since the vectors described in the present invention are created in vitro, placing new DNA sequences onto the vector is straight-forward and efficient.

SUMMARY OF THE INVENTION

The inventors have developed methods for producing large quantities of purified intact alpha satellite arrays of up to 736 kb in length. By transfecting these arrays into human cells along with telomeric DNA and human genomic DNA sequences, several wholly synthetic human chromosomes that exhibit a high degree of mitotic stability in the absence of selection have been produced.

Unlike previous approaches whereby attempts were made to produce an artificial mammalian chromosome, this approach does not rely on the modification of existing endogenous chromosomes. Furthermore, it does not produce multiple integration events within the endogenous chromosomes. These chromosomes were formed and maintained extrachromosomally, so integration into an endogenous chromosome is avoided.

The relatively high frequency of synthetic chromosome formation and the lack of other genomic rearrangements associated with the chromosome formation, allows the synthetic chromosomes made by the inventors to be used as effective vectors for heterologous gene expression and gene therapy.

The invention is thus based on the inventors' discovery that by means of isolated purified DNA alone, a synthetic or artificial chromosome is produced de novo (from purified DNA) in a cell and is produced and maintained as an extrachromosomal element. This chromosome retains the essential functions of a natural mammalian chromosome in that it is stably maintained as a non-integrated construct in dividing mammalian cells without selective pressure, just as naturally-occurring chromosomes are inherited. For a linear chromosome, this indicates centromeric, telomeric, and origin of replication functions.

The invention is thus directed to a synthetic or artificial mammalian chromosome. The chromosome is produced from isolated purified DNA. The isolated purified DNA is transfected into mammalian cells. Without integrating into an endogenous chromosome, it forms a functional chromosome. This chromosome is not derived from an endogenous naturally-occurring chromosome in situ. The starting material is isolated purified centromeric DNA and DNA that allows chromosome formation without integration. For linear chromosomes, telomeric DNA is included. In a preferred embodiment, the DNA that allows chromosome formation without integration is genomic DNA (from the naturally-occurring genome of an organism).

The artificial mammalian linear chromosome thus preferably essentially comprises centromeric, telomeric, and genomic DNA. In one embodiment, the artificial chromosome is a circular chromosome. In this case, telomeric DNA is absent since it is not necessary to replicate chromosome ends.

The genomic DNA is a subgenomic DNA fragment that is a restriction enzyme digestion fragment, a fragment produced by mechanical shearing of genomic DNA, or a synthetic fragment synthesized in vitro. The genomic DNA starting material (ie., that is transfected) can be a mixture of heterogeneous fragments (e.g., a restriction digest) or can be a cloned fragment or fragments (homogeneous).

Centromeric DNA comprises a DNA that directs or supports kinetechore formation and thereby enables proper chromosome segregation. Centromeric DNA at active, functional, centromeres is associated with CENP-E during mitosis, as demonstrated by immunofluorescence or immunoelectron microscopy. By "associated" is meant that the centromeric DNA and CENP-E co-localize by fluorescence in situ hybridization (FISH) and immunofluorescence.

Telomeric DNA comprises tandem repeats of TTAGGG that provide telomere function, i.e., replicate the ends of linear DNA molecules. Telomeric DNA is included as an optional component, to be used when linear chromosomes are desired. This is indicated herein by enclosing the terms "telomeric"/"telomere" in parentheses.

Prior to transfection, the DNA can be naked, condensed with one or more DNA-condensing agents, or coated with one or more DNA-binding proteins.

The invention is also directed to an artificial mammalian chromosome produced by the process of introducing into a mammalian cell the isolated purified DNA fragments above. In a preferred embodiment the process uses DNA essentially comprising centromeric, telomeric, and genomic DNA.

The various fragments can be transfected separately or one or more can be ligated prior to transfection. Thus the centromeric (telomeric) and genomic DNAs are introduced separately (unligated) or one or more of the isolated purified DNAs are ligated to one another.

The invention is also directed to a mammalian cell containing and compositions comprising the artificial mammalian chromosome.

The invention is also directed to the isolated purified DNA described above, and which forms an artificial mammalian chromosome when introduced into a mammalian cell. In preferred embodiments, the isolated purified DNA essentially comprises centromeric, telomeric, and genomic DNA.

The invention is also directed to a mammalian cell containing and compositions comprising the purified DNA.

The invention is also directed to a vector or vectors containing the purified DNA.

The invention is also directed to a mammalian cell containing and compositions comprising the vector(s).

The invention is also directed to the isolated purified DNA described above produced by the process of combining one or more of the DNAs described above. In preferred embodiments, the DNA includes: (1) centromeric DNA, (2) telomeric DNA, (3) genomic DNA. The DNAs can be unligated or one or more can be ligated to one another.

The invention is also directed to a method for making an artificial mammalian chromosome by introducing into a mammalian cell the purified DNA described above.

The invention is also directed to a method for making DNA capable of forming an artificial chromosome, the method comprising combining in vitro the DNA described above.

The invention is also directed to a method for propagating an artificial chromosome in mammalian cells by introducing the purified DNA into a mammalian cell and allowing the chromosome to replicate.

In a preferred embodiment, the invention is also directed to methods for expressing a heterologous gene in a mammalian cell by expressing that gene from the artificial mammalian chromosome.

Thus, the invention is also directed to methods for providing a desired gene product by including a desired gene on the artificial chromosome such that the gene of interest is expressed. In preferred embodiments, the invention provides a method of gene therapy by including heterologous therapeutic DNA on the artificial mammalian chromosome, such that there is a therapeutic effect on the mammal containing the chromosome.

In a preferred embodiment of the invention, the centromeric DNA is alpha-satellite DNA.

In a preferred embodiment of the invention, the artificial mammalian chromosome is derived entirely from human DNA sequences and is functional in human cells.

Figure 1A:
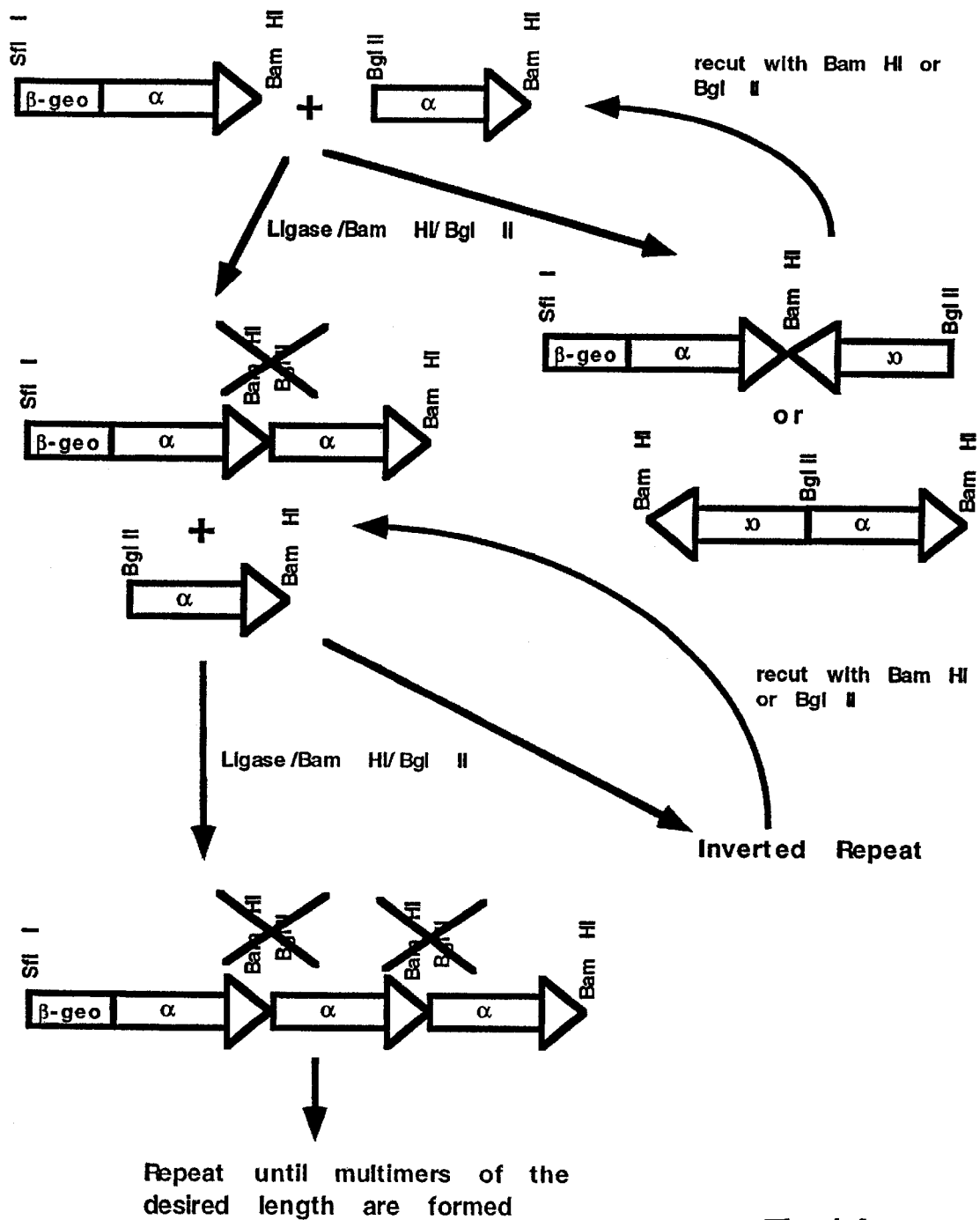
FIGS. 1A and 1B Method for producing large head-to-tail tandem arrays of alpha satellite DNA. pVJ104-Yα16 was linearized with BamHI and SfiI, and purified by pulsed field gel electrophoresis (PFGE). Likewise, pBac-Yα16 was linearized with BamHI and BglII and the alpha satellite array was purified by PFGE. A) The purified arrays were incubated together in the presence of ligase, BamHI and BglII. Since BamHI and BglII are complementary/nonisoschisomeric overhangs, a ligation event resulting in a BamHI/BglII junction (as is the case in a head-to-tail joining) will destroy both sites. Thus, a head-to-tail junction will be resistant to cleavage by BamHI and BglII. In contrast, a head-to-head, or tail-to-tail ligation event will recreate a BamHI or BglII site, respectively. Since BamHI and BglII are present, these ligation products will be cleaved to produce their constituent monomers (or head-to-tail multimers). By controlling the amount of ligase, the incubation time, and the concentration of DNA, the length of the head-to-tail products can be varied as necessary. B) Following ligation, the products were analyzed by PFGE. Lane 1, molecular weight standards (NEBL Midrange II markers); lane 2, Yα16 (BamHI/BglII fragment) ligated in the presence of BamHI and BglII for 4 hours; lane 3, Yα16

(BamHI/BglII fragment) ligated in the presence of BamHI/ BglII for 12 hours; lane 4, Yα16 (BamHI/BglII fragment) mock-ligated in the presence of BamHI and BglII; lane 5, VK75 (BssHII fragment) ligated for 12 hours without restriction enzyme; lane 6, VK75 (BssHII fragment) ligated for 12 hours in the presence of BssHII; lane 7, VK75 (BssHII fragment) mock-ligated. The molecular weight of ligation products are shown on the left. Note: Although these samples were run on the same gel, several irrelevant lanes between lanes 4 and 5 were removed.

Figure 2:
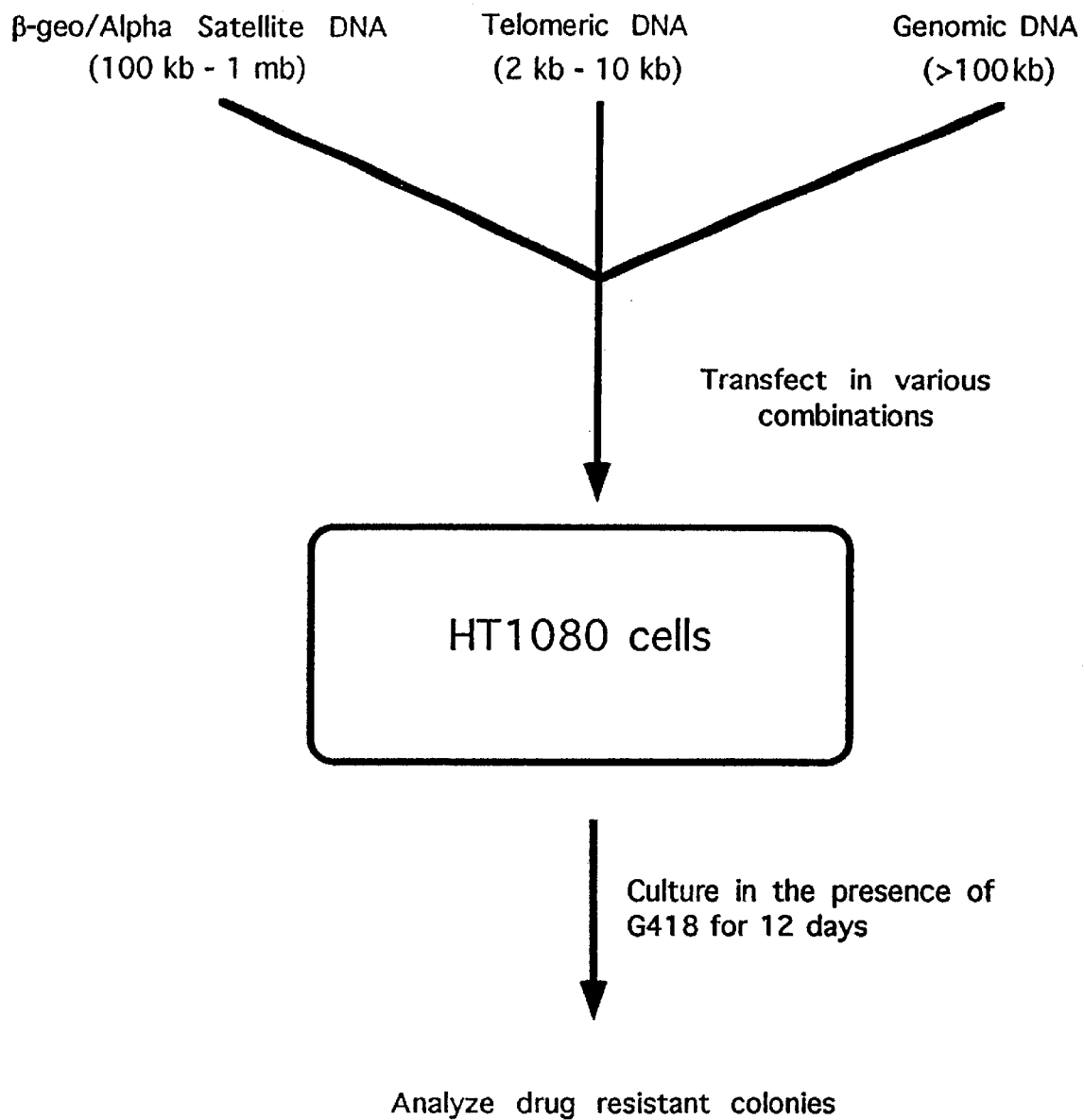
Figure 4A:
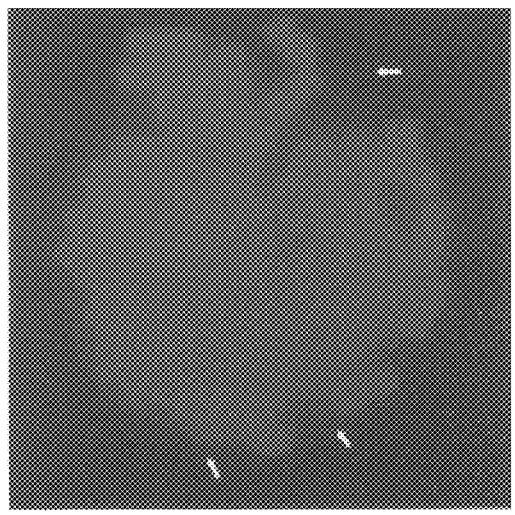
Figure 4B:
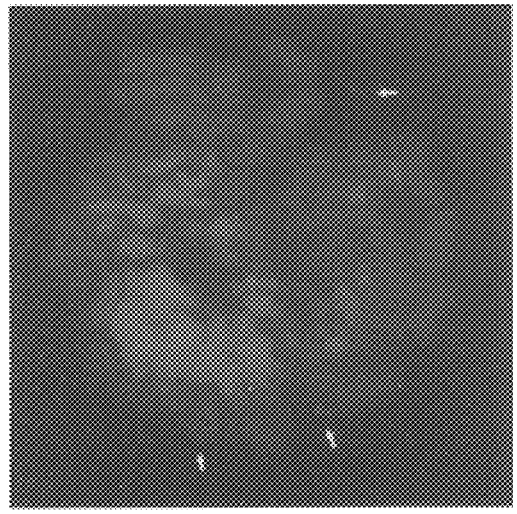
Figure 4C:
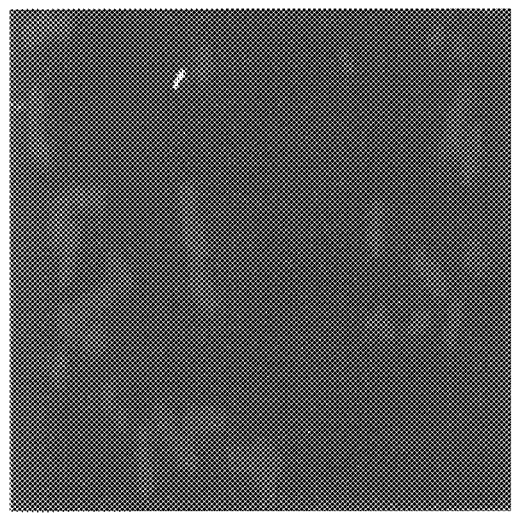
Figure 4D:
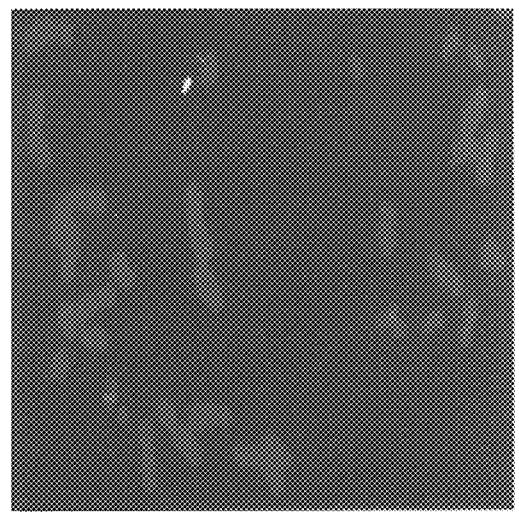

FIG. 2. Strategy for making synthetic chromosomes.

FIG. 3. Analysis of synthetic chromosomes from clones 22-7 and 22-13 by fluorescent in situ hybridization (FISH). Cells were harvested, dropped onto glass slides, and hybridized to Y alpha satellite DNA as described in the Experimental Procedures (See Examples herein). The biotinylated probe was detected using Texas Red Avidin and amplified with two layers of biotinylated anti-Avidin and Texas Red Avidin. A) DAPI image of a metaphase spread from clone 22-7. B) Same as A) except that the alpha satellite probe was visualized using a triple cube filter. C) DAPI image of a metaphase spread from clone 22-13. D) Same as C) except that the alpha satellite probe was visualized using a triple cube filter. In each case, the synthetic chromosome is indicated with a white arrow.

FIG. 4. Analysis of synthetic chromosomes from clones 22-6 and 23-1 by FISH. Cells were harvested, dropped onto glass slides, and hybridized to Y alpha satellite DNA (clone 22-6) or 17 alpha satellite DNA (clone 23-1) as described in the experimental procedures. The biotinylated probe was detected using Texas Red Avidin and amplified with two layers of biotinylated anti-Avidin and Texas Red Avidin. A) DAPI image of a metaphase spread from clone clone 22-6. B) Same as A) except that the alpha satellite probe was visualized using a triple cube filter. C) DAPI image of a metaphase spread from clone 23-1. D) Same as C) except that the alpha satellite probe was visualized using a triple cube filter. In each case, the synthetic chromosome is indicated with a white arrow. In D), the yellow arrow indicates the location of the C qter integration site.

FIG. 5. Analysis of synthetic chromosomes from clones 22-11 and 17-15 by FISH. Cells were harvested, dropped onto glass slides, and hybridized to Y alpha satellite DNA (clone 22-11) or 17 alpha satellite DNA (clone 17-15) as described in the experimental procedures. The biotinylated probe was detected using Texas Red Avidin and amplified with two layers of biotinylated anti-Avidin and Texas Red Avidin. A) DAPI image of a metaphase spread from clone clone 22-11. B) Same as A) except that the alpha satellite probe was visualized using a triple cube filter. C) DAPI image of a metaphase spread from clone 17-15. D) Same as C) except that the alpha satellite probe was visualized using a triple cube filter. In each case, the synthetic chromosome is indicated with a white arrow. In D), the yellow arrow indicates the location of the C qter integration site.

Figure 6A:
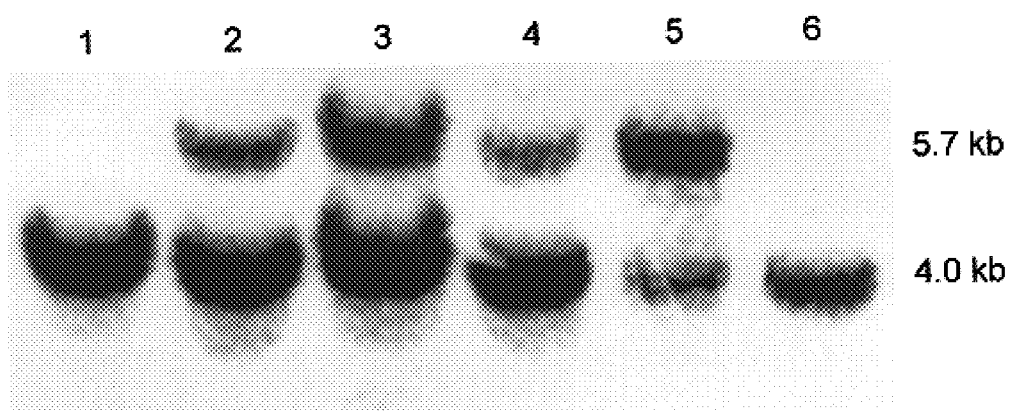
Figure 7A:
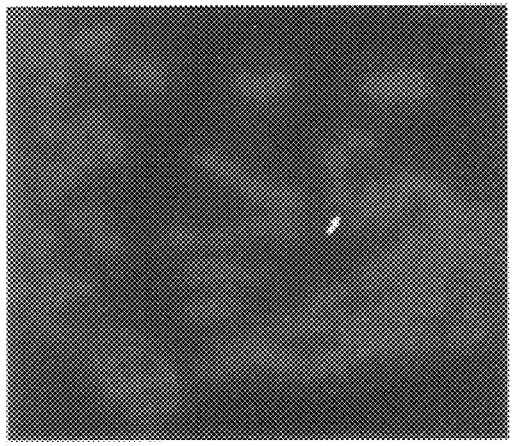
Figure 7B:
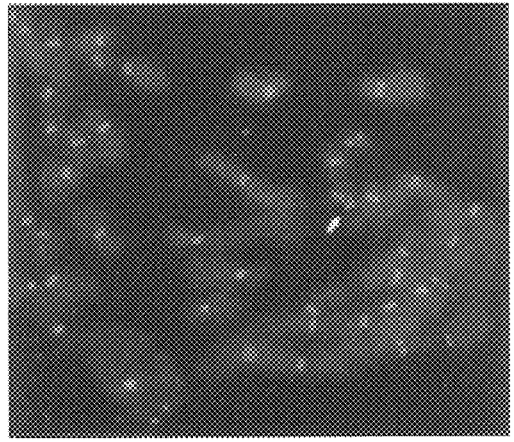
Figure 7C:
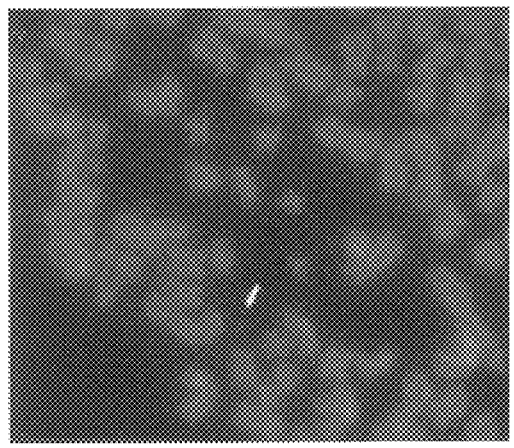
Figure 7D:
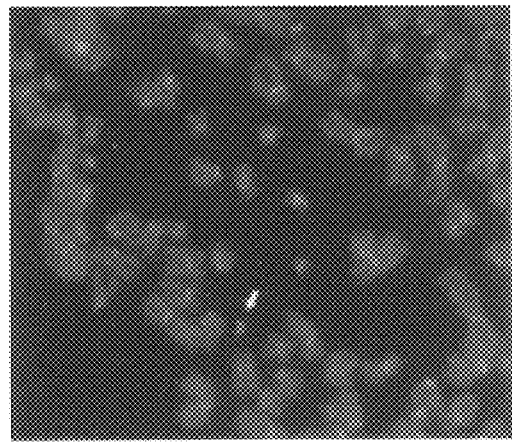

FIGS. 6A and 6B Determination of the amount of transfected alpha satellite DNA present in clones containing the synthetic chromosome. A) Total genomic DNA was harvested, digested, and electrophoresed as described in the Experimental Procedures. Lane 1, HT1080; lane 2, clone 22-6; lane 3, clone 22-7; lane 4, clone 22-11; lane 5, clone 22-13; lane 6, clone 23-1. B) The estimated amount of synthetic Y alpha satellite DNA is shown for each clone. Note: clone 23-1 was transfected with 17 alpha satellite DNA, and therefore, does not contain synthetic Y alpha satellite DNA.

FIG. 7. CENP-E is associated with the synthetic chromosomes during mitosis. Immunofluorescence was carried out on metaphase chromosomes harvested from synthetic chromosome-containing clones as described in experimental procedures. A) DAPI-stained chromosomes from clone 22-11. B) Same as A) except the location of the anti-CENP-E antibodies is visualized using a triple cube filter. C) DAPI-stained chromosomes from clone 23-1. D) Same as C) except the location of the anti-CENP-E antibodies is visualized using a triple cube filter. In each case, the synthetic chromosome is indicated by a white arrow.

Figure 8A:
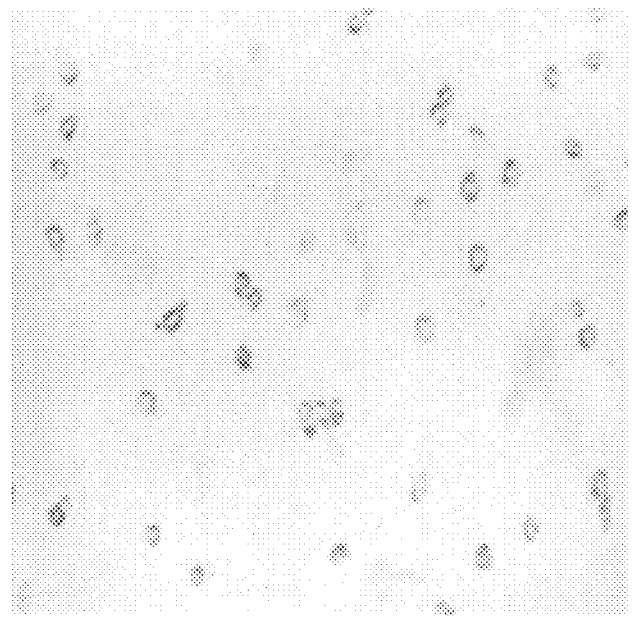
Figure 8B:
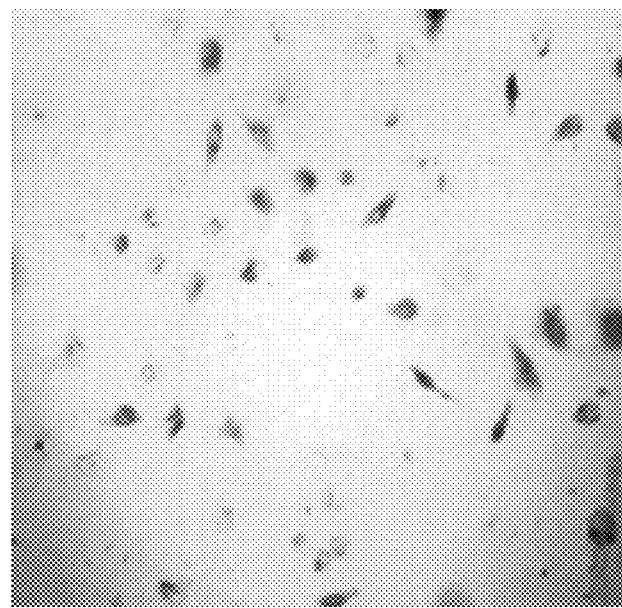

FIG. 8. X-Gal plate staining of clone 22-11 after growth for 70 days in the absence of selection. Cells were harvested and stained as described in the Experimental Procedures herein. A) HT1080 B) Clone 22-11. The presence of blue cells in clone 22-11, but not in HT1080 indicates that β-geo is still expressed in these cells.

DETAILED DESCRIPTION OF THE PREFERRED EMBODIMENTS

The inventors have discovered that functional mammalian chromosomes can be constructed from purified DNA introduced into a mammalian cell. There are several advantages to using these chromosomes for a variety of applications.

First, since they are formed and replicate autonomously, they will not result in insertional mutagenesis by inserting into the host genome.

Second, because of the large size of the transfer vector (in the megabase range), there is the capacity to accommodate the entire repertoire of a large gene including all of its regulatory elements. This itself may encompass megabases of DNA.

Third, because some genetic diseases are the result of defects in more than one gene, because of the large size of the mammalian artificial chromosome more than one gene can be accommodated.

Fourth, they are stable and can thus provide a therapeutic benefit over many cell divisions.

Fifth, they are non-immunogenic.

The invention is thus directed to a synthetic or artificial mammalian chromosome comprising essentially centromeric, genomic, and optionally, telomeric DNA. In an alternative embodiment, the artificial chromosome is a circular chromosome. In this case, telomeric DNA is absent since it is not necessary to replicate chromosome ends. The chromosome has, at the minimum, DNA sequences that provide essential chromosomal functions in a mammalian cell.

The genomic DNA is a subgenomic DNA fragment selected from the group consisting of restriction enzyme digestion fragments mechanically sheared fragments, and fragments of DNA synthesized in vitro. The genomic DNA component of the chromosome can be derived from a mixture of subgenomic fragments (e.g., a restriction enzyme digest) or from cloned fragment(s).

The function of the genomic DNA is two-fold. The DNA expresses a gene product, or causes the expression of a gene product (as, for example, by having a regulatory function), and the DNA allows the formation of an artificial chromosome from purified DNA in a cell without the integration of the purified DNA into an endogenous chromosome in the cell, the artificial chromosome also containing centromeric DNA and, optionally, telomeric DNA. The genomic DNA can be derived from any organism and can be of any size.

The genomic DNA that forms a component of the synthetic mammalian chromosome may be derived from a mammalian source other than the mammal from which the cell is derived in which the chromosome replicates. For example, mouse genomic DNA can be provided to human cells and human genomic DNA can be provided to the cells of other mammals. Further, it can be from a source different from the source of the centromere or telomere.

Still further, the function of the genomic DNA exemplified herein can be potentially carried out by genomic DNA of any organism, including procaryotic organisms, and by DNA synthesized in vitro and not corresponding to a naturally-occurring sequence, partly homologous to a naturally occurring sequence, or completely non-homologous.

Centromeric DNA essentially comprises a DNA that directs or supports kinetechore formation and thereby enables proper chromosome segregation. This centromeric DNA at active, functional centromeres is associated with CENP-E during mitosis, as demonstrated by immunofluorescence or immunoelectron microscopy. By "associated" is meant that the centromeric DNA and CENP-E co-localize by FISH and immunofluorescence.

In a preferred embodiment of the invention, the centromeric DNA is alpha satellite DNA. However, any functional centromeric DNA, and especially repetitive DNA, is enabled by the methods described herein and useful for making artificial chromosomes.

The inventors have created in vitro methods for producing large alpha satellite arrays. Previously, no method has been available allowing structurally intact alpha satellite DNA greater than 200 kb to be purified in the quantities necessary for the transfection of mammalian cells. By using these methods, controlled amounts of alpha satellite DNA can be produced in vitro. As described herein, by empirically controlling the amount of ligase, incubation time, and concentration of DNA, the length of the ultimate product can be varied as necessary.

However, the invention is not limited to centromeric DNA derived from alpha satellite DNA. The in vitro methods created by the inventors can be applied to any centromeric DNA that functions as described herein, and especially to repetitive DNA.

Further, the entire alpha satellite repeat may not be required for centromere formation. Thus, the centromeric DNA can also comprise alpha satellite derivatives and analogs, for example, sub-monomer regions in alpha satellite or related satellite DNA.

Subregions within the alphoid monomer representing protein binding sites can be ligated together to generate a functional centromere, consisting of a smaller repeat unit. The functionality of this embodiment is shown by data from mouse-human hybrids.

In the murine species *M. musculus*, minor satellite DNA contains CENP-B boxes and appears to be the functional equivalent of alpha satellite DNA. Interestingly, in *M. musculus*, the minor satellite repeat unit is only 120 bp and has no apparent sequence homology to alpha satellite DNA outside of the CENP-B box. Despite the difference in repeat size and sequence, human chromosomes segregate efficiently in mouse/human hybrids. This demonstrates that the centromeric repeat unit size and sequence can vary without destroying centromere function.

The murine species *M. caroli* apparently lacks minor satellite DNA (Kipling et al., *M. Cell. Biol.* 15:4009–4020 (1995)). In this species, the functional alpha satellite equivalent appears to be a 79 bp satellite sequence that contains a CENP-B box (there is also a 60 bp sequence that is 97% homologous to the 79 bp sequence but that lacks a CENP-B box). In crosses between *M. musculus* and *M. caroli*, chromosomes from both species segregate normally within the same cell. This shows that both the minor satellite and the 79 bp satellite sequences are recognized by the same spindle during mitosis. Thus, different centromeric repeat sizes can be functional.

Since alpha satellite, minor satellite, and 79 bp satellite repeats are different sizes and are functional, the absolute repeat size per se is not the determinant of functionality of centromeric DNA. Additionally, since there is only limited sequence homology between these centromeric repeats, it is likely that subregions within the repeats representing protein binding sites are the important functional component.

Thus, in one embodiment of this invention, the centromeric DNA contains subregions within alpha satellite DNA. In a preferred embodiment, the centromeric DNA is composed of tandemly ligated CENP-B boxes, defined by the sequence 5'aTTCGttggAaaCGGGa3'(SEQ ID NO:1), where the bases indicated by capital/bold letters are the most important for CENP-B binding and the bases indicated by lower case letters may be substituted with other bases.

In other embodiments, alphoid equivalents from other species are used for centromeric DNA Human and other mammalian chromosomes have been shown to segregate efficiently in cells from other species as demonstrated by interspecies somatic cell hybrids. Examples of these hybrids include mouse×human, hamster×human, rat×human, hamster×mouse, rat×mouse, and chicken×human. The stability of a human chromosome in chicken cells (Dieken, E., et al., *Nature Genet.* 12:174–182 (1996)) shows that human centromeric DNA is also functional in a non-mammalian species (i.e., avian).

Based on observations from cross-species hybrids, it is clear that chromosomes from one species are functional in other species. Therefore, synthetic chromosomes can be produced in human cells using centromeric repeats from other mammals (and avians) instead of, or in conjunction with, alpha satellite DNA. Conversely, alpha satellite DNA can be used as the source for centromeric DNA in other mammalian (and avian) species.

Thus, in a further embodiment of the invention, genomic (telomeric) DNA is transfected into cells along with *M. musculus* minor satellite DNA, *Mus caroli* 79 bp satellite DNA, or analogous sequences from other mammals. In another embodiment, telomeric and genomic DNA is transfected into cells along with centromeric DNA from avian cells.

Essentially, centromeric DNA that is associated with CENP-E during mitosis is embodied in the aspect of the invention that encompasses the use of centromeric sequences heterologous to the host cell and other synthetic chromosomal components. As long as the centromeric sequence in the chromosome is associated with CENP-E during mitosis, a functional chromosome for mammalian cells would be expected to result irrespective of the genomic sequence(s) and telomere sequences, and for that matter, irrespective of the specific centromeric sequence.

The telomeric DNA can be derived from any DNA sequence (from any desired species) that retains a telomeric function. In mammals and other vertebrates, the most abundant and conserved sequence at the chromosome end is TTAGGG, which forms arrays between 2 and 20 kilobases in length. Human telomere DNA consists of about 5 kilobases of the repeat TTAGGG, and small stretches of this sequence are enough to seed telomere formation after introduction of linear molecules into mammalian cell lines (Huxley, C., *Gene Ther.* 1:7–12 (1994)). Simple (TTAGGG)$_n$ arrays are sufficient to provide the telomere function required by an artificial chromosome. The telomeric DNA, therefore, comprises tandem arrays of the hexamer TTAGGG. Telomeric DNA is included when the formation of linear chromosomes is desired.

Telomeres, centromeres and replication origins are discussed in Huxley, C. et al., *Biotechnol.* 12:586–590 (1994).

The invention is also directed to purified DNA molecules that essentially comprise centromeric, genomic, and optionally, telomeric DNA, as described herein.

In one embodiment, the purified DNA is naked DNA.

In another embodiment, the purified naked DNA is condensed with one or more agents that condense DNA. It may be advantageous to condense the purified DNA prior to transfection in order to stabilize it against shearing. By condensing the purified centromeric (telomeric) and genomic DNA prior to transfection, it will become more resistant to structural insult arising from manipulations during transfection. Thus, in one embodiment of this invention, the purified centromeric (telomeric) and genomic DNA is condensed with one or more DNA condensing agents prior to transfection. In this respect, polycations have been shown to physically condense high molecular weight DNA and to protect it from mechanical shearing (Kovacic et al., *Nucleic Acids Res.* 23:3999–4000 (1995); Widom and Baldwin, *J. Mol. Biol.* 144:431–453 (1980); Widom and Baldwin, *Biopolymers* 22:1595–1620 (1983)). Therefore, in a further embodiment, the purified DNA is condensed with polycationic compounds. Examples of polycationic compounds include poly-lysine, poly-arginine, spermidine, spermine, and hexaminecobalt chloride.

In an alternative embodiment, the invention encompasses precoating DNA with proteins. It may also be advantageous to precoat the DNA with DNA-binding proteins such as histones, nonhistone chromosomal proteins, telomere binding proteins, and/or centromere binding proteins. This precoating is expected to have several desirable consequences. First, it will result in condensation of the DNA which will protect the high molecular weight DNA from shearing. Second, it will inhibit nuclease degradation of the transfected DNA by blocking nucleases from binding to the DNA. Third, the precoated DNA may enter the nuclease more efficiently following transfection, since each of the proteins listed above contain nuclear localization signals. By precoating the centromeric (telomeric) and genomic DNA with DNA binding proteins prior to transfection, we expect to increase the efficiency of transfection and synthetic chromosome formation.

Thus, in another embodiment of this invention, the purified centromeric (telomeric) and genomic DNA is coated with DNA binding proteins prior to transfection. Examples of DNA-binding proteins include histones, non-histone chromosomal proteins, transcription factors, centromere binding proteins, and telomere binding proteins.

DNA-binding proteins can also be identified and purified by their affinity for DNA. For example, DNA binding may be revealed in filter hybridization experiments in which the protein (usually labeled to facilitate detection) is allowed to bind to DNA mobilized on a filter or, vice-versa in which the DNA binding site (usually labeled) is bound to a filter upon which the protein has been immobilized. The sequence specificity and affinity of such binding is revealed with DNA protection assays and gel retardation assays. Purification of such proteins may be performed utilizing sequence-specific DNA affinity chromatography techniques, for example column chromatography with a resin derivatized with the DNA to which the domain binds. Proteolytic degradation of DNA-binding proteins may be used to reveal the domain which retains the DNA binding ability.

The invention is thus directed to an artificial mammalian chromosome produced by the process of transfecting a mammalian cell with the purified DNA, described herein, and allowing the cell to completely reconstitute the DNA in vivo.

The invention is thus directed to an artificial mammalian chromosome produced by the process of transfecting a mammalian cell with purified naked DNA, the DNA comprising essentially centromeric DNA (telomeric DNA) and genomic DNA, as described herein.

The invention is thus also directed to an artificial chromosome produced by the process of transfecting a mammalian cell with purified condensed DNA, the DNA comprising essentially, centromeric DNA (telomeric DNA), and genomic DNA, as described herein.

The invention is thus also directed to an artificial mammalian chromosome produced by the process of introducing purified coated DNA into a mammalian cell, the DNA comprising essentially a centromere (a telomere) and genomic DNA, as described herein.

The invention is also directed to purified DNA made by the process of combining, in vitro, isolated purified and genomic DNA (telomeric DNA) as described herein.

The invention is also directed to purified, condensed DNA made by the process of combining, in vitro, isolated purified centromeric DNA (telomeric DNA) and genomic DNA, as described herein. Alternatively, the individual DNA components could be pre-condensed and then combined.

The invention is also directed to purified, coated DNA made by the process of combining, in vitro, isolated purified centromeric DNA (telomeric DNA) and genomic DNA, as described herein and adding DNA-binding proteins. Alternatively, the individual DNA components could be pre-coated and then combined.

The purified DNA described above may comprise unligated centromeric (telomeric) and genomic DNA. Alternatively, the purified DNA described above can also comprise centromeric (telomeric) and genomic DNA in which one or more of these DNAs are ligated to each other.

The invention is also directed to a composition comprising the purified DNA described above. The composition may contain components that facilitate the entry of the DNA into a cell. For the formation of an artificial chromosome, the composition may facilitate the uptake of the DNA into a mammalian cell. Alternatively, the composition may comprise ingredients that facilitate the uptake of the DNA into a cell which is used for propagation of a vector containing the DNA.

The invention is also directed to a vector containing the DNA described above. The vector may be used for propagating the DNA, i.e., amplifying the sequences described above prior to introducing them into a mammalian cell and forming an artificial chromosome.

Accordingly, the invention is also directed to a composition comprising the vector containing the DNA described above.

The invention is also directed to a cell containing the vector described above.

The invention is also directed to a mammalian cell containing the artificial chromosome.

The invention is also directed to a mammalian cell containing the purified DNA described above.

Although any mammalian cell is encompassed by the invention, in preferred embodiments of the invention, the mammalian cell is a human cell.

In preferred embodiments of the invention, the centromeric DNA is human alpha satellite DNA. It is understood, however, that alpha satellite DNA may be derived from any primate. The invention further encompasses centromeric DNA from non-primate mammals, wherein said centromeric DNA is associated with CENP-E during mitosis. Any centromeric DNA that is associated with CENP-E during mitosis, and especially repetitive DNA, irrespective of the organism from which it is derived, is expected to provide functional centromeric sequences for an artificial mammalian chromosome according to the present invention. Thus, an artificial mammalian chromosome that functions in human cells, for example, may contain centromeric sequences derived not from humans but from non-human mammals and even from non-mammalian species such as avians. Any repetitive DNA that is associated with CENP-E is potentially useful. Accordingly, following the methods taught herein, any centromeric sequence can be tested for function as a component of a mammalian artificial chromosome.

In specific disclosed embodiments of the invention, the centromeric DNA comprises large stretches of alpha satellite array, a segment composed of the repeating telomeric sequence $(TTAGGG)_n$ and random genomic fragments produced by digestion with the restriction enzyme NotI. In preferred embodiments, the restriction enzyme digests DNA into pieces in the range of fragments generated by NotI digestion of human genomic DNA and preferably in the range of 10 kb to 3 mb. This includes but is not limited to BamHI, BglI, SalI, XhoI, SfiI, NotI, SrfI, PmeI, and AscI.

When the purified DNA is introduced into a mammalian cell, this DNA forms a functional synthetic or artificial chromosome. This chromosome has the characteristics of a naturally-occurring mammalian chromosome. The chromosome is present in the cell at a low copy number, usually one per cell. The chromosome is linear and contains telomeric sequences. CENP-E is associated with the artificial chromosome during mitosis, indicating the formation of a functional kinetechore. The chromosome is mitotically stable in the absence of selection. The chromosome is structurally stable with time with an undetectable integration frequency. The chromosome contains one or more transcriptionally active genes. Thus, these chromosomes do not originate from naturally-occurring chromosomes but are constructed starting in vitro from isolated purified DNA sequences.

Accordingly, the invention is also directed to a method for making an artificial mammalian chromosome, the method comprising introducing into a mammalian cell the purified DNA described above.

The DNA can be introduced into the mammalian cell by any number of methods known to those in the art. These include, but are not limited to, electroporation, calcium phosphate precipitation, lipofection, DEAE dextran, liposomes, receptor-mediated endocytosis, and particle delivery. The chromosomes or DNA can also be used to microinject eggs, embryos or ex vivo or in vitro cells. Cells can be transfected with the chromosomes or with the DNA described herein using an appropriate introduction technique known to those in the art, for example, liposomes. In a preferred embodiment of the invention, introduction of purified DNA into the mammalian cell is by means of lipofection.

The purified DNA is thus useful for transfecting a mammalian cell, said transfecting resulting in the formation of an artificial chromosome in the cell from the transfected DNA.

The DNA can be propagated in non-mammalian cells separately or where one or more of the components is ligated together. Thus, the invention is also directed to the purified DNA ligated into a vector for propagation. Such vectors are well-known in the art and include, but are not limited to, pBac/108L, P1, pACYC184, pUC19, pBR322, YACs, and cosmids.

The invention is also directed to a mammalian cell containing the artificial or synthetic chromosome. The invention is directed to any mammalian chromosome or mammalian cell. Although all mammals are encompassed, the preferred embodiment is the human. A preferred embodiment of the invention therefore encompasses a human cell containing a synthetic human chromosome.

The DNA and chromosomes have been developed especially for use as expression vectors for gene therapy and other purposes. Therefore, in preferred embodiments of the invention, the purified DNA also consists essentially of one or more DNA sequences useful for the expression of a desired gene product, for example, as therapeutic agents. The invention is thus directed to a method for introducing expressible DNA into a cell by including this DNA on the artificial chromosome. The DNA can be regulatory, structural, expressed as a gene product, and the like. In a preferred embodiment, the DNA provides a gene product. When transfected into mammalian cells, the artificial chromosomes that are formed following transfection harbor and express these DNA sequences.

Recombinant DNA technology has been used increasingly over the past 20 years for the production of desired biological materials. DNA sequences encoding a variety of medically important human gene products have been cloned. These include insulin plasminogen activator, α1 antitrypsin, and coagulation factors. The present invention, however, encompasses the expression of any and all desired medically and/or biologically relevant gene products.

Once in the cell, the heterologous gene product is expressed in the tissue of choice at levels to produce functional gene products. The general consensus is that correct tissue-specific expression of most transfected genes is achievable. For correct tissue specificity, it may be important to remove all vector sequences used in the cloning of the DNA sequence of interest prior to introduction into the cell and formation of the artificial chromosome. Thus, the heterologous gene of interest can be incorporated into the artificial chromosome in a controlled manner so that the naturally-occurring sequences are present in their naturally-occurring configuration, and tissue specificity is assured.

Synthetic chromosomes can be introduced into human stem cells or bone marrow cells. Other applications will be clear to those of skill in the art.

A variety of ways have been developed to introduce vectors into cells in culture and into cells in tissues of an animal or human patient. Methods for introducing vectors into mammalian and other animal cells include calcium phosphate transfection, the DEAE-dextran technique, micro-injection, liposome-mediated techniques, cationic lipid-based techniques, transfection using polybrene, protoplast fusion techniques, electroporation, and others. These techniques are well known to those of skill in the art, and are described in many readily available publications and been extensively reviewed. Some of the techniques are reviewed in *Transcription and Translation, A Practical Approach*, Hames, B. D. & Higgins, S. J., eds., IRL Press, Oxford (1984), herein incorporated by reference for their relevant teachings, and *Molecular Cloning,* 2nd Edition, Maniatis et al., Cold Spring Harbor Laboratory Press, Cold Spring Harbor, N.Y. (1989), herein incorporated by reference for its relevant teaching.

In the description, reference has been made to various methodologies known to those of skill in the art of molecular biology. Publications and other materials setting forth such known methodologies to which reference is made are incorporated herein by reference for their relevant teachings.

A standard reference work setting forth the general principles of recombinant DNA technology is Maniatis, T. et al., *Molecular Cloning: A Laboratory Manual,* 2nd Edition, Cold Spring Harbor Laboratory, Cold Spring Harbor, N.Y. (1989).

Definitions

All terms pertaining to recombinant DNA technology are used in their art-recognized manner and would be evident to one of ordinary skill in the art.

The terms "Y alpha satellite" and "Yα" are used interchangeably and refer to alpha satellite DNA derived from the Y chromosome.

The terms "17 alpha satellite" and "17α" are used interchangeably and refer to alpha satellite DNA derived from chromosome 17.

Alpha satellite DNA is a tandemly-repeated DNA sequence present at human centromeres and that comprises a basic monomeric repeat of approximately 170 bps. This small repeat is organized into higher order units that have been shown to be specific to one or a small group of human chromosomes.

The term "centromeric" means that region of the chromosome that is constricted and is the site of attachment of the spindle during meiosis or mitosis. It is necessary for the stability and proper segregation of chromosomes during meiosis and mitosis and is therefore an essential component of artificial chromosomes. Centromeric DNA comprises a DNA that directs or supports kinetochore formation and thereby enables proper chromosome segregation. Centromeric DNA at active, functional, centromeres is associated with CENP-E during mitosis, as demonstrated by immunofluorescence or immunoelectron microscopy. By "associated" is meant that the centromeric DNA and CENP-E co-localize by FISH and immunofluorescence.

"Essential chromosome functions" are discussed in the description and background above. These include mitotic stability without experimental selective pressure, substantially 1:1 segregation, autonomous replication, i.e., centromere, telomere, and origin of replication functions.

The term "functional equivalent" denotes a genetic function that arises from a different DNA or protein sequence, but which provides the same biological function.

The term "gene product" denotes a DNA, RNA, protein or peptide.

The term "genomic DNA" encompasses one or more cloned fragments or fragments from a restriction digest or other mixture of sequences and sizes, for example mechanically sheared DNA, or DNA synthesized in vitro. The DNA could be derived from the same chromosome (as, for example, when cloned fragments are used or when DNA from a purified chromosome is digested) or from different chromosomes (as, for example, when a genomic restriction digest is used for transfection).

The term "genomic" refers to DNA naturally found in the genome of an organism. However, the inventors also recognize that the function of this genomic DNA could be carried out by DNA from other sources, for example, synthetic DNA that has a sequence not found in nature. Thus, as used herein, "genomic" DNA is also used generically to refer to the DNA that is introduced into a cell along with the centromeric (telomeric) DNA described herein, and which DNA expresses a gene product, or causes expression of a gene product, and allows the formation, in a cell, of a chromosome from purified DNA without the integration of the purified DNA into an endogenous chromosome in the cell. This DNA could thus be synthetic or derived from any organism and can be of any size as long as it contains the requisite expressible sequence and the function discussed above.

Therefore, in addition to the centromeric DNA, the artificial chromosome that is encompassed in the invention essentially contains DNA sequences that express a gene product, or causes expression of a gene product, and that allows the formation of a chromosome from purified DNA without the integration of the purified DNA into an endogenous chromosome in the cell. The sequence that functions to provide the chromosomal expression (e.g., non-integration) and the expression sequence can be the same sequence. Thus, it is within the contemplation of the inventors that the expressible sequence also provides the other functions. Alternatively, the sequence that provides the chromosomal function and the expression function may be different sequences and from different sources.

In a specific disclosed embodiment, the genomic DNA is derived from a Not I restriction digest. Therefore, in a preferred embodiment, DNA that allows the formation of a chromosome from purified DNA without the integration of the purified DNA into an endogenous chromosome is derived from a restriction fragment generated by the digestion of total genomic DNA with a restriction enzyme having the recognition cite (8 nucleotides) of Not I. However, it is well within the contemplation of the inventors to use restriction fragments and other fragments of naturally-occurring genomic DNA, that are smaller than those generated by Not I and comparable enzymes. For example, the inventors contemplate reducing the size of the DNA while retaining the functions above. Therefore, in a highly preferred embodiment, the DNA is pared down to contain only the DNA necessary to provide for the expression of one or more genes of interest and to provide the function of allowing the formation of the chromosome from purified DNA without prior integration of the purified DNA into an endogenous chromosome.

The source of these DNAs need not be the same. Thus, the expression sequence can be derived from one organism and the sequence that provides the chromosomal function can be from another organism. Further, one or both sequences can be synthesized in vitro and need not correspond to naturally occurring sequences. In this respect, the sequences need not strictly be "genomic". The only restriction on the sequences is that they provide the functions indicated above.

The term "heterologous" denotes a DNA sequence not found in the naturally-occurring genome in which cell the artificial mammalian chromosome is introduced. Additionally, if the sequence is found, additional copies are considered "heterologous" because they are not found in that form in the naturally-occurring genome. As discussed above, the heterologous DNA can simultaneously be the desired expression sequence(s) and the "genomic DNA". "Expressible" DNA may not itself be expressed but may allow or cause the expression of another DNA sequence, heterologous or endogenous. This is the case if the DNA is regulatory, for example.

The term "mammalian chromosome" means a DNA molecule or genetic unit that functions as a chromosome in a mammalian cell.

The term "naked DNA" means DNA that is unassociated with any of the biological (chromosomal or cellular) components with which it is normally associated in a naturally-occurring chromosome, for example histones, non-histone chromosomal proteins, RNA, transcription factors, etopoisomerases, scaffold proteins, centromere-binding proteins, and telomere-binding proteins. Such DNA can be isolated from cells and purified from the non-DNA chromosomal components. Alternatively, this DNA can be synthesized in vitro.

The term "naturally-occurring" denotes events that occur in nature and are not experimentally-induced.

An origin of replication indicates a site of initiation of DNA synthesis.

The term "isolated" refers to DNA that has been removed from a cell. The term "purified" refers to isolated DNA that has been substantially completely separated from non-DNA components of a cell or to DNA that has been synthesized in vitro and separated substantially completely from the materials used for synthesis that would interfere with the construction of the chromosome from the DNA A purified DNA can also be a DNA sequence isolated from the DNA sequences with which it is naturally associated.

A replicon is a segment of a genome in which DNA is replicated and by definition contains an origin of replication.

The phrase "retains all the functions of a natural mammalian chromosome" means that the chromosome is stably maintained in dividing mammalian cells as a non-integrated construct, without experimental selective pressure, indicating at least centromeric, telomeric (for linear chromosomes), origin of replication functions, and gene expression.

The term "stable" denotes that the synthetic or artificial chromosome remains present in at least 50% of the cells after ten generations in the absence of experimental selective pressure (such as drug selection and the like), and most preferably, that after 30 generations, it is present in at least 10% of the cells; and preferably, the synthetic chromosome exhibits 1:1 segregation greater than 99% of the time.

The terms "synthetic" or "artificial" are used interchangeably. A "synthetic" or "artificial chromosome" is a construct that has essential chromosome functions but which is not naturally-occurring. It has been created by introducing purified DNA into a cell. Since the chromosome is composed entirely of transfected DNA, it is referred to as synthetic or artificial. An artificial or synthetic chromosome is found in a configuration that is not naturally-occurring.

The term "transfecting" denotes the introduction of nucleic acids into a cell. The nucleic acid thus introduced is not naturally in the cell in the sequence introduced, the physical configuration, or the copy number.

A telomere denotes the end of a chromosome comprising simple repeat DNA that is synthesized by a ribonucleoprotein enzyme called telomerase. The function is to allow the ends of a linear DNA molecule to be replicated.

A nucleic acid molecule such as a DNA or gene expresses a polypeptide or gene product if the molecule contains the sequences that code for the polypeptide and the expression control sequences which, in the appropriate host environment, provide the ability to transcribe, process and translate the genetic information contained in the DNA in a protein product and if such expression control sequences are operably linked to the nucleotide sequence which encodes the polypeptide. However, as discussed herein, a gene product need not be restricted to a polypeptide gene product but may encompass RNA. Further, genetic defects that are capable of being corrected by the artificial mammalian chromosomes when used as expression vectors may be defects that operate in cis to effect further gene expression.

An operable linkage is a linkage in which the regulatory DNA sequences and the DNA sequence sought to be expressed are connected in such a way as to permit gene expression. The precise nature of the regulatory regions needed for gene expression may vary from organism to organism but in general include a promoter region, 5' non-coding sequences involved with initiation of transcription and translation such as the TATA Box, CAP Sequence, CAAT Sequence, and the like. If desired, the non-coding region 3' to the gene sequence coding for the protein may be obtained by the above-described methods. This region may be retained for its transcriptional termination regulatory sequences such as termination and polyadenylation. Thus, by retaining the 3' region naturally contiguous to the DNA sequence coding for the protein, the transcription termination signals may be provided. Where the transcriptional termination signals are not satisfactorily functional in the expression host cell, then a 3' region functional in the host cell may be substituted.

The following examples do not limit the invention to the particular embodiments described, but are presented to particularly describe certain ways in which the invention may be practiced.

Examples

Experimental Procedures

Description of DNA Constructs

Standard molecular biology techniques were used to construct all plasmids described here (Sambrook, J. et al., eds., "Molecular Cloning", Cold Spring Harbor Laboratory Press (1989)). Cloning of the alpha satellite higher order repeat from the Y chromosome and chromosome 17 has been described previously (Wolfe, J. et al., *J. Mol. Biol.* 182:477–485 (1985); Van Bokkelen, G. B. et al., "Method for Stably Cloning Large Repeating Units of DNA", U.S. Patent Application(1995)); Waye & Willard, *M. Cell. Biol.* 6:3156–65 (1986)). By directional cloning through the creation of the appropriate restriction sites, successively larger alpha satellite arrays have been created in the plasmid pBAC108L Van Bokkelen, G. B. et al., "Method for Stably Cloning Large Repeating Units of DNA", U.S. patent application Ser. No. 08/487,989, filed Jun. 7, 1995, now U.S. Pat. No. 5,695,967 which is incorporated herein by reference for teaching the cloning of large tandem arrays of repetitive sequences.

Plasmids Used in the Experiments pBAC108L has been described previously (Shizuya, H. et al., *Proc. Natl. Acad. Sci. USA* 4 89:8794–7 (1992)). pVJ105 is a modified version of pBAC108L that contains additional restriction sites in the polylinker and a β-geo expression unit consisting of the CMV immediate early gene promoter and SV40 polyadenylation signal (Seed, B., *Nature* 329:840–2 (1987); Seed & Aruffo, *Proc. Natl. Acad. Sci. USA* 84:3365–9 (1987)), the β-geo open reading frame (MacGregor, G. R. et al., *Development* 121:1487–96 (1995)), and the UMS transcriptional termination sequence (Heard, J. M. et al., *M. Cell. Biol.* 7:2425–34 (1987); McGeady, M. L. et al., *DNA* 5:289–98 (1986); Salier & Kurachi, *Biotechniques* 7:30–1 (1989)). pBACYα16 (92 kb of Y alpha satellite) consists of 16 identical higher order repeats cloned head-to-tail into pBAC108L. pBAC17α32 (87 kb of 17 alpha satellite) consists of 32 identical higher order repeats cloned head-to-tail into pBAC108L. pVJ105-Yα16 was made by cloning the alpha satellite array from pBAC108L into pVJ105. Following linearization with BamHI and SfiI, the direction of β-geo expression is toward the alpha satellite array. pVJ105-17α32 was made by cloning the alpha satellite array from pBAC17α32 into pVJ105. Following linearization as above, the direction of β-geo transcription is toward the alpha satellite array. All plasmids were purified by alkaline lysis (Sambrook, J. et al., eds., "Molecular Cloning", Cold Spring Harbor Laboratory Press (1989)) followed by agarose gel purification.

Creation of Alpha Satellite Arrays>100 kb by Multimerization

To create Y alpha satellite arrays, pVJ105 Yα16 was digested with BamHI and SfiI and gel purified by pulsed field gel electrophoresis (PFGE). Additional alpha satellite DNA was prepared by digesting pBACYα16 with BamHI and BglII and gel purifying the 92 kb alpha satellite fragment by PFGE as above. Following band isolation, the agarose bands were equilibrated in 10 mM Tris pH 7.5, 100 mM NaCl, 10 mM $MgCl_2$ and then melted at 65° for 5 minutes. The two fragments were then combined at a molar ratio of 5:1 (pBACYα16 alpha satellite fragment: pVJ105-Yα16 fragment). ATP (1 mM final) and T4 Ligase (5 units) were added and the reaction was incubated at 37° C. for 4 hours in the presence of BamHI (40 units) and BglII (40 units). β agarase (3 units) was added and the reaction was incubated at 37° C. for 1 hour. The reaction was then placed on ice for 1 hour prior to transfection into HT1080 cells. To create extended alpha satellite arrays for 17 alpha satellite DNA, the above procedure was used with pVJ105-17α32 and pBAC17α32 in place of pVJ105-Yα16 and pBAC17α32, respectively.

Preparation of High Molecular Weight Human Genomic DNA

Four 150 mm plates containing HT1080 cells were grown to confluency, removed from the plates with trypsin/EDTA, and washed with 100 ml PBS. High molecular weight DNA was harvested in low gelling temperature agarose plugs (Sambrook J. et al., eds., "Molecular Cloning", Cold Spring Harbor Laboratory Press (1989)). Approximately 1 μg of human genomic DNA was digested with NotI. Following digestion, NotI was inactivated by heating the reaction to 70° C. for 5 min. Prior to transfection, the agarose plug was digested with 3 units of β-agarase.

Preparation of telomeric DNA

Human telomeric DNA was generated by PCR using primers 42a (5'GGGTTAGGGTTAGGGTTAGGGTTA GGGTTAGGGTTAGGG3')(SEQ ID NO: 2)and 42b (5'CCCTAACCCTAACCCTAACCCTAACCCTAACCCT AACCC3')(SEQ ID NO: 3) (Ijdo, J. W. et al., *Nucleic Acids Res.* 19:4780 (1991)). Each PCR reaction contained 250 ng of 42a and 42b, 5 Units Taq polymerase, 250 μM dNTPs, 3.3 mM $MgCl_2$ in 1×PCR Buffer (Gibco BRL). The PCR reaction was carried out for 35 cycles in a Perkin Elmer 9600 Thermal cycler using the following temperature profile: 95° C. for 20 seconds, 40° C. for 20 seconds, 72° C. for 2 minutes. Following PCR, each reaction was subjected to agarose gel electrophoresis to purify telomeric DNA that is greater than 1 kb in size. This DNA was excised from the gel and purified away from the agarose using Magic Prep columns according to the manufacturer's instructions (Promega, Wis.).

Transfection of Human cells

Prior to transfection, pVJ105 Yα16 and pVJ105 17α32 were digested with BamHI and SfiI; pBac Yα16 and pBac Yα32 were digested with BamHI and BglII. The DNA was then purified by PFGE, equilibrated against 10 MM Tris pH 7.5, 100 mM NaCl, and combined with telomeric DNA and/or NotI digested human genomic DNA. In some cases, the alpha satellite arrays were extended using the directional ligation approach described in FIG. 1.

Once the DNA components for each transfection were combined and gently mixed. Transfections contained either pVJ105 Yα16 (0.5–1 μg), pVJ105 17α32 (0.5–1 μg), or pVJ105 VK75 (0.5–1 μg). Where indicated, the transfections also contained purified Yα16 arrays (0.5–1μg), 17α32 arrays (0.5–1 ug) telomeric DNA (75–250 ng), human genomic DNA (1–3 μg) and/or VK75 fragment (0.5–2 μg). 1 ml serum free α-MEM media (MediaTech) was added. 7.5 μl lipofectin was then added, and the solution was incubated at room temperature for 5 minutes. The DNA:lipofectin mixture was added to 2×106 HT1080 cells, according to the manufacturer's instructions (Gibco BRL). After a 16 hour incubation at 37° C., the DNA:lipofectin solution was removed and complete media was added to the cells. At 36 hours post transfection, the cells were removed from the wells with trypsin/EDTA and transferred to a 100 mm plate containing complete media supplemented with 300 μg/ml G418. On the seventh day of selection, the media was replaced with fresh complete media supplemented with 300 μg/ml G418. After 12 days of selection, individual colonies were isolated using sterile cloning rings and placed into 24 well plates. The individual clones from each transfection were then expanded under selection into 100 mm plates. A portion of each culture was frozen for future analysis, while the bulk was harvested for analysis by FISH.

Cell Culture

HT1080 cells were grown in Alpha MEM media (Gibco/BRL, Bethesda, MD) supplemented with 15% fetal bovine serum (Hyclone), penicillin/streptomycin, and glutamine. The subclone of HT1080 used in these experiments was tetraploid.

Plate Staining

Cells containing the synthetic chromosomes were plated in 6 well plates at 10% confluency. Untransfected HT1080 cells were similarly plated and used as a negative control. When the cells reached 70% confluency, the media was removed and the cells were washed with 2 ml PBS. After removing the PBS, 1 ml of fix solution (2% formaldehyde, 0.2% glutaraldehyde in PBS) was added to each well and the plate was incubated at room temperature for 4 minutes. The fix solution was removed and the cells were immediately washed with 2 ml PBS. Finally, PBS wash was removed and 1 ml of staining solution (5 mM potassium ferricyanide, 5 mM potassium ferrocyanide, 5 mM $MgCl_2$, and 1 μg/μl X-Gal in PBS) was added to each well and the plate was incubated for 12 hours at 37° C. The cells were washed with PBS and imaged using a light microscope and associated imaging hardware (Oncor, Gaithersburg, Md.).

Fluorescence in Situ Hybridization

HT 1080 cells were grown on 100 mm tissue culture plates, harvested for FISH and mounted onto slides according to published procedures (Verma, R. & Babu, A., *Human Chromosomes, Principles and Techniques*, 2nd Edition, McGraw-Hill, Inc. (1995)). To detect alpha satellite sequences on the synthetic chromosomes and on the endogenous chromosomes, chromosome specific alpha satellite probes were used according to manufacturers instructions (Oncor, Gaithersburg, Md.).

Determination of Synthetic Y Alpha Satellite DNA Content in Clones Containing Synthetic Chromosomes Genomic DNA was harvested from HT1080 cells and from clones 22-6, 22-7, 22-11, 22-13, and 23-1 according to published procedures (Sambrook, J. et al., eds., *Molecular Cloning*, Cold Spring Harbor Laboratory Press, Cold Spring Harbor, N.Y. (1989)). Approximately 10 μg DNA from each clone was then digested with EcoRI (50 units) and PstI (50 units) overnight at 37° C. The samples were then electrophoresed through a 0.8% agarose gel, transferred to Nytran membrane, and hybridized to a 1 kb Y alpha satellite probe in 25% formamide/10% dextran/0.5% SDS/0.5M NaCl/200 μg/ml salmon sperm DNA overnight at 65° C. EcoRI and PstI both cleave once in the endogenous Y alpha satellite higher order repeat to give a 4 kb and a 1.7 kb band. However, due to the method used to create the synthetic Y alpha satellite arrays, EcoRI does not cleave the synthetic higher order repeat. As a result, EcoRI and PstI digestion of the synthetic array results in a 5.7 kb band. Since we know that the endogenous Y alpha satellite array is 1 mb in length, we can determine the amount of synthetic alpha satellite DNA in the cells containing synthetic chromosomes by determining the ratio of the 5.7 kb band (synthetic array) to the 4.0 kb band (endogenous array). It is not necessary to consider the 1.7 kb band since it does not hybridize with the probe under these hybridization conditions. It is important, however, to consider that most of these clones contain 2 Y chromosomes (because they are tetraploid) and only a single synthetic chromosome. One exception to this is clone 22-13 which contains a single Y chromosome and appears to be diploid. Thus, for clones 22-6, 22-7, and 22-11, the amount of synthetic alpha satellite DNA per cell is estimated by the following equation:

$$\frac{\text{Intensity of 5.7 kb band}}{\text{Intensity of 4 kb band}} \times 1\text{ mb} \times 2$$

For clone 22-13, the following equation was used:

$$\frac{\text{Intensity of 5.7 kb band}}{\text{Intensity of 4 kb band}} \times 1\text{ mb}$$

Immunofluorescence

Anti-CENP immunofluorescence was carried out according to published procedures (Sullivan & Schwartz, *Hum. Mol. Genet.* 4:2189–2197 (1995)). Briefly, HT1080 cells were grown in tissue culture plates until approximately 80% confluency. Colcemid was then added to a final concentration of 40 ng/ml and the cells were incubated at 37° C. for 75 minutes. The media was carefully removed and the cells were released from the plate by incubation with trypsin/EDTA for 3 to 5 minutes. To neutralize the trypsin, complete media was added to the cells and the resulting cell suspension was counted using a hemocytometer and spun at 1000 rpm in a Jouan CT422 centrifuge. The supernatent was discarded and the cells were resuspended at $0.6 \times 10^5$ cells/ml by slowly adding hypotonic solution (25 mM KCl, 0.27% sodium citrate). Cells were incubated in hypotonic solution for 12 minutes at room temperature. 500 μl of cells were then added to a cytofunnel and spun at 1900 rpm for 10 minutes in a Shandon Cytospin 3 centrifuge. The slides were then incubated in 10 mM Tris pH 7.7, 120 mM KCl, 20 mM NaCl, 0.1% Triton X-100 for 12 minutes. Diluted antibody (50 μl, 1/1000 in 1 mM triethanolamine, 25 mM NaCl, 0.2 mM EDTA, 0.5% Triton X-100, 0.1% BSA) was added to each slide and a plastic cover slip was positioned over the cells. Following a 30 minute incubation at 37° C., the coverslip was removed, and the slides were washed 3×2 minutes in a Coplin jar containing KB (10 mM Tris pH 7.7, 150 mM NaCl, 0.1% BSA). FITC-labeled anti-rabbit Ig was added (50 μl of 1/100 in KB) and a plastic cover slip was placed over the cells. Following a 30 minute incubation at 37° C., the slides were washed 3×2 minutes in a Coplin jar containing KB. Before viewing, the slides were counterstained with 10 μl DAPI (2 μg/ml in antifade). Images were collected using a fluorescent microscope and imaging system (Oncor, Gaithersburg, Md.).

Mitotic Stability Time Course

Following cloning, cells were expanded into two 100 mm plates and grown in the presence of 300 μg/ml G418. At 80% confluency, one plate for each clone was harvested for FISH analysis using the protocol described above. These cells serve as the time zero point of the time course. The other plate was split 1/16 into a 100 mm plate and grown to confluency in complete media lacking G418. As soon as the culture reached confluency, the cells were split 1/16 and grown in complete media lacking G418. This process was repeated for the period of time indicated in Table 2. At various time points, a portion of the culture was harvested for FISH and analyzed for the presence of the transfected alpha satellite (17α or Yα). For each intact chromosome spread, the number of Y alpha satellite (or 17 alpha satellite) signals and their chromosomal positions were determined.

Results

The mammalian centromere is a complex chromosomal element thought to consist of large blocks of repetitive DNA, called alpha satellite. One of the major impediments inhibiting the elucidation of mammalian centromere structure and preventing the development of artificial human chromosomes has been the inability to clone large segments of this class of DNA. Recently, methods for the cloning and large scale production of alpha satellite DNA up to approximately 175 kb in length have been developed (Van Bokkelen, G. B. et al., entitled "Method for Stably Cloning Large Repeating Units of DNA" U.S. application Ser. No. 08/487,989, filed Jun. 7, 1995 now U.S. Pat. No 5,695,962. Equally important, the use of a directional cloning strategy allows the creation of alpha satellite arrays of known composition and structure.

Figure 1B:
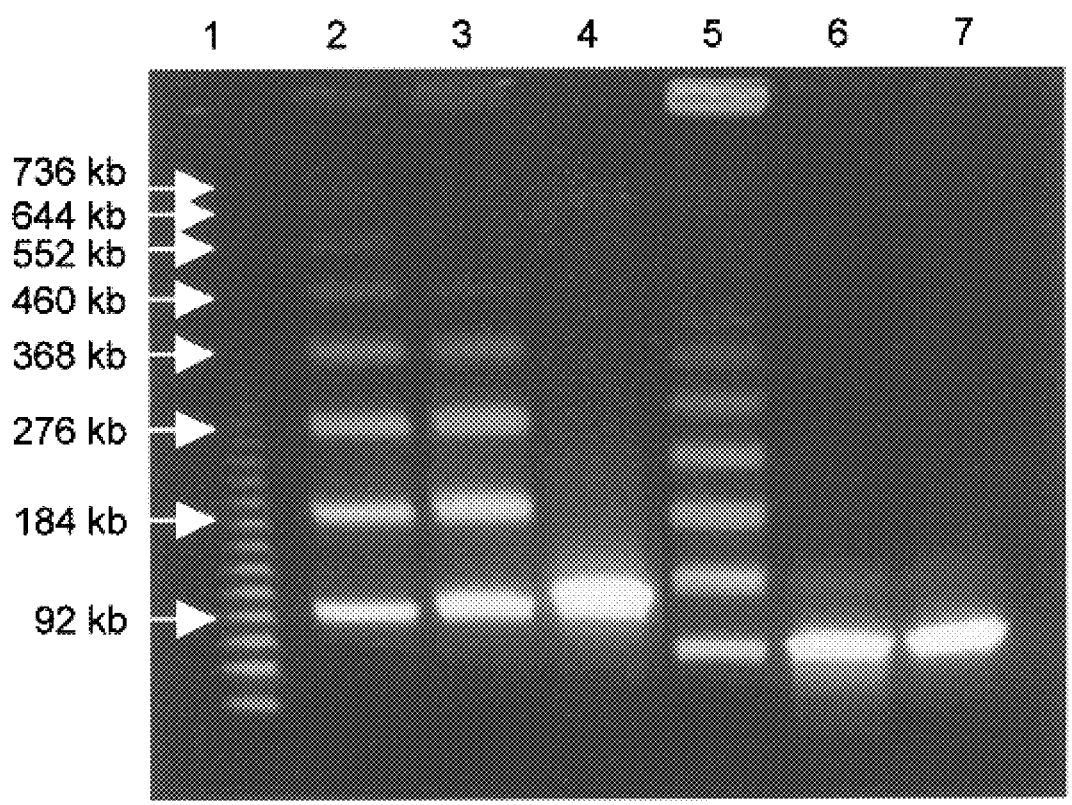

In order to facilitate the formation of a functional centromere from naked transfected alpha satellite DNA, the inventors hypothesized that it could be advantageous to transfect alpha satellite DNA which is greater than 175 kb in size. Previously, the largest contiguous alpha satellite array to be transfected into mammalian cells was 120 kb (Larin, Z. et al., *Hum. Mol. Genet.* 3:689–95 (1994)). To produce alpha satellite DNA much larger than 175 kb, the directional ligation strategy shown in FIG. 1A was used. This in vitro technique allows the production of contiguous, uninterrupted Y alpha satellite arrays up to 736 kb in length (FIG. 1B, lanes 2–4). As a control, VK75 (a 75 kb BssHII fragment) was ligated in the presence and absence of BssHII (FIG. 1B, lanes 5–7). Since BssHII ends regenerate a BssHII site when ligated, the ladder of multimers is digested down to constituent monomers when BssHII is included in the ligation reaction. Similar results were obtained in experiments carried out using BamHI fragments or BglII fragments (data not shown). This demonstrates that the recleavage reaction is efficient and that the ladder in lanes 2 and 3 are the result of head-to-tail ligations. Finally, to test for biological differences between separate families of alpha satellite DNA, extended arrays were also built consisting of alpha satellite DNA derived from chromosome 17 (data not shown).

The inventors have utilized these large purified alpha satellite arrays to produce synthetic chromosomes using the strategy outlined in FIG. 2 and described in Experimental Procedures. By cotransfecting each of these chromosome components, the inventors reasoned that the cell would combine these elements to form a functional chromosome. Accordingly, HT1080 cells were transfected with various combinations of alpha satellite DNA, telomeric DNA, and human genomic DNA. Following transfection, the cultures were placed under G418 selection for 10–14 days. Individual colonies were then isolated, expanded under selection, and harvested for FISH analysis.

Characterization of Stable Transfectants

As shown in Table 1, in clones from the majority of transfections, alpha satellite DNA had integrated into an endogenous chromosome. In many transfections that included telomeric DNA, a high incidence of alpha satellite integration events associated with chromosome truncations was observed also. It has been observed previously that telomeric DNA can be used to efficiently truncate human chromosomes following integration (Barnett, M. A. et al., *Nucleic Acids Res.* 21:27–36 (1993); Brown, K. E. et al., *Hum. Mol. Genet.* 3:1227–37 (1994); Farr, C. J. et al., *EMBO J.* 14:5444–54 (1995)). Here, telomeric DNA apparently integrated into the endogenous chromosome along with alpha satellite DNA and caused a truncation event.

In cells from a subset of transfections, however, synthetic chromosomes that contained the transfected alpha satellite DNA were observed (Table 2, transfections 22 and 23 and FIGS. 3–5). These positive transfections differed from the other transfections in two ways. First, prior to transfection, the alpha satellite DNA was preligated in vitro in the presence of BamHI and BglII (FIGS. 1A and 1B). This resulted in the generation of large, directional alpha satellite arrays ranging in size from 100 kb to 736 kb in length. Second, NotI digested human genomic DNA was included in the transfection. By including these two components, the essential DNA sequences necessary for synthetic chromosome formation were provided.

FISH analysis of clones from transfections 22 and 23 revealed that approximately 50% of the G418 resistant clones contained synthetic chromosomes (Table 1). In four of the five synthetic chromosome containing clones from these two transfections, the transfected alpha satellite DNA was detectable only on the synthetic chromosome (FIGS. 2–4). That is, in the case of transfected Y alpha satellite DNA, only the synthetic chromosome and the Y chromosome had detectable signals by FISH. Likewise, in the case of transfected 17 alpha satellite DNA, only the synthetic chromosome and chromosome 17 had detectable signals for 17α by FISH. Interestingly, synthetic chromosomes formed in both transfections 22 and 23. This demonstrates that alpha satellites from the Y chromosome and from chromosome 17 are both capable of facilitating synthetic chromosome formation. As further evidence that alpha satellite DNA is an important component of the synthetic chromosomes, the alpha satellite FISH signal encompasses most or all of each synthetic chromosome.

Figure 5A:
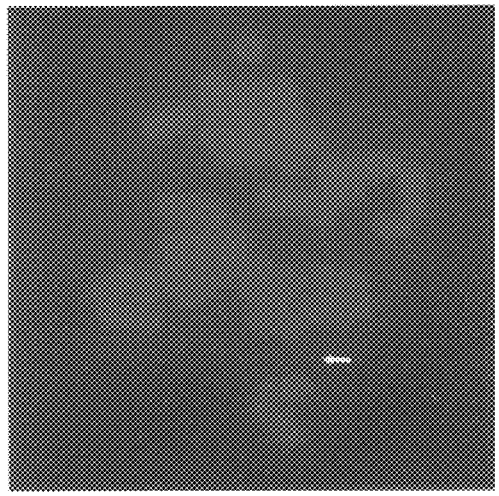
Figure 5B:
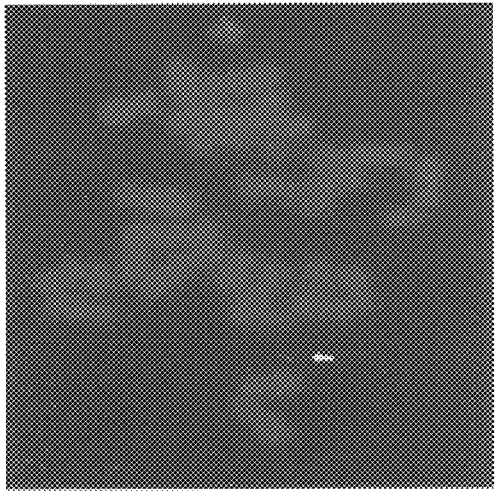
Figure 5C:
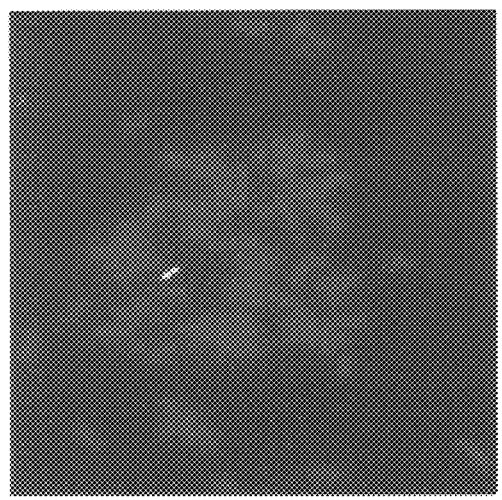
Figure 5D:
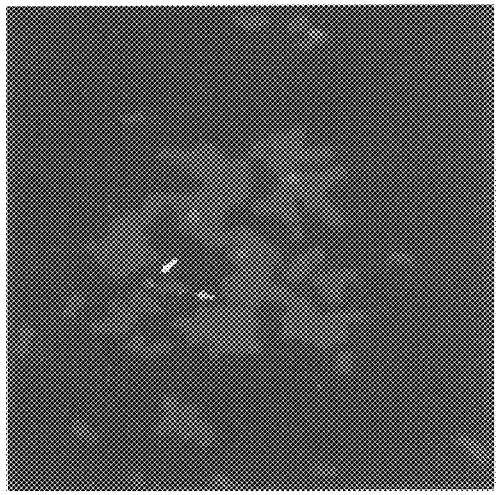

In cells that contain a synthetic chromosome, there were only two exceptions where alpha satellite DNA (derived from the same chromosome as the synthetic a satellite DNA used in the transfection) was detected on a chromosome other than the synthetic chromosome and Y chromosome (or chromosome 17 in cases where 17 a satellite was transfected). First, in clone 17-15, 17 alpha satellite DNA was detected on the synthetic chromosome, chromosome 17, and at the end of a C group chromosome (FIGS. 5A and B). Interestingly, this transfection contained unligated alpha satellite and telomeric DNA, but no human genomic DNA. One possibility is that the transfected DNA integrated into the endogenous chromosome, amplified, and broke back out. It is important to note that if non-alphoid, non-telomeric human sequences are necessary for chromosome function, then this mechanism of synthetic chromosome formation might be necessary to provide additional DNA elements in the absence of human genomic DNA in the transfection. In the one case in which a synthetic chromosome formed in the absence of cotransfected human genomic DNA, alpha satellite was also found integrated into an endogenous chromosome. This shows that genomic DNA is necessary for some aspect of synthetic chromosome formation or maintenance. Second, in clone 22-11, both a synthetic chromosome and a Y: 14 chromosome translocation were observed (FIGS. 5C and D). By pulsed field gel electrophoresis, the inventors have demonstrated that the Y: 14 translocation contains endogenous Y alpha satellite DNA, and not synthetic Y alpha satellite DNA. Thus, the synthetic alpha satellite DNA is only detectable on the microchromosome, and not on any endogenous chromosome.

Estimation of Synthetic chromosome Size

The amount of alpha satellite DNA present in the synthetic chromosome containing cells ranges from about 350 kb to 2 mb (FIG. 6). This was determined by taking advantage of restriction site polymorphisms between the 5 synthetic and endogenous alpha satellite arrays. By comparing the intensity of the synthetic alpha satellite band to the endogenous alpha satellite band on a Southern blot, the ratio of synthetic alpha satellite DNA to endogenous alpha satellite DNA can be determined. Since the endogenous alpha satellite array is 1 mb in length (Larin et al., *Hum. Mol. Genet.* 3:689–95 (1994)), and since the copy number of the Y chromosome (2 for clones 22-6, 22-7, and 22-11 and one for clone 22-13) and the copy number of the synthetic chromosome are known (Table 2), the amount, in kilobases, of synthetic alpha satellite DNA (FIG. 5B) can be estimated.

Although it is difficult to estimate the overall size of these synthetic chromosomes, in some cases, the synthetic chromosome is barely detectable using a fluorescence microscope at 1000x magnification.

Synthetic Chromosome Structure and Copy Number

Upon initial analysis, each clone of synthetic chromosome containing cells possessed very few synthetic chromosomes, and in most cases, only one per cell. This shows that the copy number of the synthetic chromosomes is regulated like that of the endogenous chromosomes.

In addition to copy number, the synthetic chromosomes share two other features with the endogenous chromosomes. First, they contain telomeric sequences (data not shown). This suggests that these synthetic chromosomes are linear. Second, in metaphase chromosomes, the individual chromatids are clearly visible on each synthetic chromosome (FIGS. 4–5). This shows that the overall structure of the synthetic chromosome is similar to that of the endogenous chromosomes. Furthermore, since chromatids are normally held together at the centromere, this result also shows that the synthetic chromosomes are capable of carrying out at least one centromeric function, the attachment of sister chromatids.

CENP-E Associates with Synthetic Chromosomes During Metaphase

The presence of synthetic chromosomes (in most cases at single copy) in dividing cells shows the creation of a functional centromere. In order to further investigate this, several of the synthetic chromosomes were tested to determine whether CENP-E was present at the centromere during metaphase. It has been shown previously that CENP-B is present at both functional and nonfunctional centromeres (Earnshaw, W. C. et al., Chromosoma 98:1–12 (1989)), and therefore, it can not be used as a marker for centromere activity. For this reason, CREST antisera (used in previous experiments: Haaf et al., Larin et al., and Praznovsky et al. (cited above)), which generally recognizes CENP-B very strongly, is not a good reagent for assessing centromere activity. On the other hand, CENP-E has been shown to be present only at functional centromeres (Sullivan & Schwartz, Hum. Mol. Genet. 4:2189–2197 (1995)), and therefore, monospecific antibodies to this protein can be used to assess centromere activity.

Consistent with the presence of a functional centromere, it was found that CENP-E was present on the synthetic chromosome in clones 22-11 and 23-1, the only clones tested to date (FIG. 7). Furthermore, the amount of CENP-E on the synthetic chromosome is similar to that present at the centromere of each of the endogenous chromosomes. This is interesting because CENP-E is not thought to bind to centromeric DNA directly, and therefore, its level does not depend on the amount of alpha satellite present. Instead, it depends solely on whether a functional kinetochore has formed. Thus, the presence of CENP-E on the synthetic chromosome during metaphase strongly suggests that they contain a functional centromere capable of directing formation of a centromere/kinetochore complex.

Synthetic Chromosomes are Mitotically Stable in the Absence of Selection

To confirm that the synthetic chromosomes contain a functional centromere and are capable of correctly segregating in dividing cells, the synthetic chromosome containing cells were grown for a defined period of time in the absence of selection. The cells were then analyzed by FISH to determine the percentage of cells that contained the synthetic chromosome. After 46 days (approximately 60 cell generations) in the absence of selection, the synthetic chromosomes were still present in the majority of cells (Table 2). In several clones, the synthetic chromosome was still present in 100% of the cells. This indicates that the synthetic chromosomes are mitotically stable, and therefore, validates the idea that these vectors can be used to transfect dividing cells to correct genetic defects in vivo.

In addition to determining the segregation efficiency of each synthetic chromosome, this experiment also allowed us to assess the structural stability of the synthetic chromosomes over time. After scanning 50 chromosome spreads for each clone, no cases in which the synthetic chromosome integrated into an endogenous chromosome were observed. Furthermore, no other gross rearrangements involving the synthetic chromosomes were observed. This result, in conjunction with their high degree of mitotic stability, demonstrates that these synthetic chromosomes behave as separate genetic units with many of the same characteristics as endogenous human chromosomes.

Gene Expression from the Synthetic Chromosomes

The synthetic chromosomes described here provide an alternative vector for somatic gene therapy. It is, therefore, important to determine whether heterologous genes can be efficiently expressed from these chromosome vectors.

As described in the experimental procedures, the synthetic chromosomes were created by co-transfecting pVJ104-Yα16 or pVJ104-17α32 with telomeric DNA and human genomic DNA into HT1080 cells. In each transfection, the β-geo expression unit was linked to at least 100 kb of alpha satellite DNA. Following transfection, the location of alpha satellite in the cell is the same as the location of the β-geo gene. Thus, in the synthetic chromosome clones, with the exception of clone 17-15, the β-geo gene is located exclusively on the synthetic chromosome.

To determine the levels of β-geo expression in each of the synthetic chromosome containing clones, and therefore the extent of gene expression from the synthetic chromosome, the cells were assayed using the X-gal plate staining method described in the experimental procedures. Although this technique is relatively insensitive (i.e. β-geo expression must be high in order to be detected), it provided a rough approximation of expression levels and the percentage of cells expressing this marker gene. After 70 days in culture without G418 selection (approximately 80 cell divisions), at least 50% of the cells in clones 22-11 expressed β-geo at levels detectable in this assay (FIG. 8). In clone 22-6, approximately 25% of the cells had detectable β-geo activity after 70 days in the absence of selection (data not shown). Expression in the other clones could not be evaluated due to the insensitivity of this assay and due to the lower expression of β-geo in these cells.

Discussion

The results show that naked DNA can be transfected into mammalian cells and, without integrating into an endogenous chromosome, form a functional synthetic chromosome. These synthetic chromosomes have many of the characteristics of normal mammalian chromosomes. First, they are present in the cell at low copy number, usually one per cell. Second, the synthetic chromosomes appear to be linear and contain telomeric sequences. Third, during mitosis, CENP-E is bound to the synthetic chromosome indicating the formation of a functional kinetochore. Fourth, the synthetic chromosomes are mitotically stable in the absence of selection. Fifth, the synthetic chromosomes are capable of harboring transcriptionally active genes. Finally, the synthetic chromosomes are structurally stable over time, with an undetectable integration frequency. Unlike normal human chromosomes, the synthetic chromosomes are small and easily manipulated allowing different genes to be expressed in a variety of chromosomal contexts.

The results show in vitro methods for producing alpha satellite arrays up to 736 kb in length. In addition to providing an essential component to the synthetic chromosomes described here, these results demonstrate that alpha satellite can be produced in clinically useful quantities. Previously, there has been no method available allowing structurally intact alpha satellite DNA greater than 200 kb to be purified in the quantities necessary for the transfection of mammalian cells.

As a control, the inventors recreated the previous failed experiments of Haafet. et al., creating a chromosome with the concomitant integration of a satellite DNA into an endogenous chromosome. The transfection in which this occurred lacked additional genomic DNA sequences. Without genomic sequences, it is very likely that the chromosome formed as a result of a breakage event from one of the endogenous chromosomes that contain integrated alpha satellite DNA. In addition to being an inefficient and infrequent event, this approach is not useful for gene therapy procedures due to the risk of inducing genomic rearrangement and malignant transformation in the host cell as a result of the chromosome breakage mechanism.

In summary, the inventors have demonstrated that mitotically stable synthetic chromosomes can be created by transfecting large alpha satellite arrays, telomeric DNA, and genomic DNA together into a human cell. Although each of these components appears to be necessary for efficient synthetic chromosome formation, it is possible that genomic rearrangements following integration of alpha satellite DNA can lead to chromosome formation in the absence of genomic (non-alpha satellite, non-telomeric) sequences. On the other hand, alpha satellite DNA appears to be absolutely required to produce these synthetic chromosomes. Here, by creating synthetic chromosomes using alpha satellite derived from the Y chromosome and from chromosome 17, the inventors have demonstrated that the source of alpha satellite DNA is not important. In other words, alpha satellite DNA from any chromosome can be used to create synthetic chromosomes. Furthermore, given that human chromosomes are stable in a variety of hybrids, including mouse, hamster, and primate, alpha satellite-like sequences from these other species can also be used to create synthetic chromosomes such as those described here.

TABLE 1

| Clone | Yα | 17α | hg | tel | VK75 | Characteristics |
|---|---|---|---|---|---|---|
| C10-7 | XX | | | X | | Integrant (mid-Q of a large chromosome) |
| C10-10 | XX | | | X | | Integrant (mid arm-medium size chromosome) |
| C11-7 | | X | | X | | Integrated (forms a 17p+) |
| C11-19 | | X | | X | | no signal |
| C12-2 | | XX | | X | | no signal |
| C12-3 | | XX | | X | | no signal |
| C12-5 | | XX | | X | | Integrated (mid arm) |
| C12-6 | | XX | | X | | Integrated (non-telomeric) |
| C12-14 | | XX | | X | | no signal |
| C12-16 | | XX | | X | | no signal |
| C13-1 | | | | X | X | Integrated |
| C14-1 | X | | | X | X | Telomere directed truncation |
| C15-2 | X | | | X | | Chr. 6 trancation; de novo telomere |
| C15-3 | X | | | X | | no signal |
| C15-4 | X | | | X | | Integrated (p arm of a 16 like chrom) |
| C15-5 | X | | | X | | no signal |
| C15-10 | X | | | X | | Integrated into a telocentric chromosome |
| C15-12 | X | | | X | | Integrated into chrom 17 below centromere |
| C15-13 | X | | | X | | no signal |
| C15-21 | X | | | X | | no signal |
| C16-6 | XX | | | X | | Telomeric/telocentric p-constriction |
| C16-7 | XX | | | X | | no signal |
| C17-2 | | X | | X | | no signal |
| C17-8 | | X | | X | | no signal |
| C17-11 | | X | | X | | truncation of C group chromosome |
| C17-15 | | X | | X | | microchromosome, truncation of C |
| C17-19 | | X | | X | | no signal |
| C19-1 | X | | X | X | | no signal |
| C19-2 | X | | X | X | | Ambiguous (telomere directed truncation?) |
| C21-1 | | | | X | X | no signal |
| C22-2 | (XX) | | | X | X | Chr. truncation (de novo |

TABLE 1-continued

| Clone | Yα | 17α | hg | tel | VK75 | Characteristics |
|---|---|---|---|---|---|---|
| | | | | | | telomere @ 19p) |
| C22-3 | (XX) | | | X | X | no signal |
| C22-4 | (XX) | | | X | X | Telomeric/Possible dicentric |
| C22-5 | (XX) | | | X | X | Ambiguous; very small micro? |
| C22-6 | (XX) | | | X | X | Double micro (multiple micro) |
| C22-7 | (XX) | | | X | X | Large micro |
| C22-8 | (XX) | | | X | X | Ambiguous (possible micro) |
| C22-9 | (XX) | | | X | X | Telomeric/large array |
| C22-11 | (XX) | | | X | X | Small micro |
| C22-13 | (XX) | | | X | X | Large micro |
| C23-1 | | (XX) | | X | X | Small micro |

Results from the transfection of various combinations of alpha satellite DNA, telomeric DNA, and human genomic DNA into human cells.
Yα and 17α are abbreviations for alpha satellite from the Y chromosome and chromosome 17, respectively.
hg is an abbreviation for human genomic DNA that was digested with NotI.
Tel is an abbreviation for telomeric DNA.
VK75 is an abbreviation for a 75 kb fragment from the X chromosome.
X indicates that a sequence was included in the transfection.
XX indicates that additional purified alpha satellite DNA was included in the transfection, as described in the Experimental Procedures.
(XX) indicates that additional alpha satellite DNA was preligated to the b-geo/alpha satellite construct prior to transfection, as described in the Experimental Procedures.

TABLE 2

| CLONE | t = 0 days | t = 10 days | t = 20 days | t = 46 days |
|---|---|---|---|---|
| 22-7 (Y) | 10 cells: 2 Ys | 10 cells: 2 Ys (7 cells) | 10 cells: 2 Ys (9 cells) | 10 cells: 2 Ys (8 cells) |
| Micro-chromosome | 1 micro-chromosome 100% | 1 micro-chromosome 100% | 1 micro-chromosome 100% | 1 micro-chromosome 100% |
| 22-11 (Y) | 20 cells: 2 Ys (17 cells) | 10 cells: 2 Ys (6 cells) | 10 cells: 2 Ys (8 cells) | 10 cells: 2 Ys (5 cells) |
| Micro-chromosome | t (Y; 14) (19 cells) 0 micro-chromosome (7 cells) | t (Y; 14) (9 cells) 13 p+ (8–9 cells) | t (Y; 14) (10 cells) 13 p+ (8 cells) | 1 Y (4 cells) 0 Y (1 cell) |
| | 1 micro-chromosome (12 cells) | 1 micro-chromosome (2 cells) | 0 micro-chromo-somes* (2 cells) | 0 micro-chromo-somes (5 cells) |
| | 2 micro-chromo-somes (1 cell) 65% | 2 micro-chromo-somes (1 cell) 100% | 1 micro-chromo-some (2 cells) 2 micro-chromo-somes (5 cells) 3 micro-chromo-somes (1 cell) ?80+% | 1 micro-chromo-some (2–3 cells) 2 micro-chromo-somes (2 cells) 40–50% |
| 22-13 (Y) | 17 cells: 1 Y | 10 cells: 1 Y | 10 cells: 1 Y | 10 cells: 1 Y |
| Micro-chromosome | 1 micro-chromosome 100% | 1 micro-chromosome 100% | 1 micro-chromosome 100% | 1 micro-chromosome 100% |
| 23-1 (17) | 11 cells: 4–17s | 10 cells: 4–17s | 10 cells: 4–17s | 10 cells: 4–17s |
| Micro-chromosome | 1 micro-chromosome 100% | 1 micro-chromosome 100% | 1 micro-chromosome 100% | 100% |

TABLE 2-continued

| CLONE | t = 0 days | t = 10 days | t = 20 days | t = 46 days |
|---|---|---|---|---|
| 17-15 (17) | 17 cells: 4–17s (15 cells) | N.D. | 10 cells: 4–17s | N.D. |
| Micro-chromosome | 1 Cqter (10 cells) 1 micro-chromosome 100% | | 1 Cqter (6 cells) 1 micro-chromosome 100% | |
| 22-6 (Y) | 9 cells: 2 Ys | 10 cells: 2 Ys | 10 cells: 2 Ys (7 cells) | N.D. |
| Integrated signals | 1 metacent, huge sig. (2 cells) 1 D-like w/ signal (2 cells) | 1 metacent, huge sig. (2 cells) 1 D-like w/ signal (1 cell) | 1 metacent, huge sig. (5 cells) 1 E-like (?) w/ signal (1 cell) | |

Table 2. The synthetic chromosome is mitotically stable in the absence of selection. Each clone was grown in the absence of selection for the indicated number of days. Following this culture period, the cells were harvested for FISH and hybridized to the appropriate alpha satellite probe as described in the Experimental Procedures herein. For each time point, the number of cells analyzed, the number of Y chromosomes (or the number of number 17 chromosomes in the cases of clone 23-1 and 17-15), and the number of synthetic chromosomes are indicated. In addition, the percentage of cells containing a synthetic chromosome is shown in bold for each time point. The time points 0, 10, and 20 days correspond to 0, 12, and 24 cell divisions, respectively.

What is claimed is:

1. An artificial mammalian chromosome comprising DNA, said chromosome prepared by a process comprising:
   a) mixing:
      i) a composition comprising purified DNA fragments comprising telomeric DNA;
      ii) a composition comprising purified DNA fragments comprising centromeric DNA wherein said centromeric DNA is a directional, repetitive array at least 100 kb in length of either alpha-satellite DNA or sequences functionally equivalent to alpha-satellite DNA from other mammals and avians; and
      iii) a composition comprising purified mammalian genomic DNA that has been fragmented;
   b) introducing the mixture produced in step (a) into a mammalian cell in vitro; and
   c) propagating said cell under conditions that allow the formation of said artificial mammalian chromosome in said cell of the mixture.

2. An artificial mammalian chromosome comprising:
   a) centromeric DNA comprising a directional, repetitive array at least 100 kb in length of either alpha-satellite DNA or sequences functionally equivalent to alpha-satellite DNA from mammals or avians;
   b) telomeric DNA; and
   c) a subgenomic-fragment of mammalian DNA obtained by a process comprising:
      1) mixing: a) a composition comprising purified DNA fragments comprising said centromeric DNA; b) a composition comprising purified DNA fragments comprising the telomeric DNA; c) a composition comprising purified mammalian genomic DNA that has been fragmented;
      2) introducing the mixture produced in step (1) into a mammalian cell in vitro; and
      3) propagating said cell under conditions that allow the formation of an artificial mammalian chromosome comprising the sub-genomic fragment in said cell from the DNA fragments of the mixture.

3. A process for preparing an artificial mammalian chromosome comprising:
   a) mixing:
      i) a composition comprising purified DNA fragments comprising centromeric DNA which comprises a directional, repetitive array at least 100 Kb in length of either alpha-satellite DNA or sequences functionally equivalent to alpha-satellite DNA from mammals or avians;
      ii) a composition comprising purified DNA fragments comprising telomeric DNA; and
      iii) a composition comprising purified mammalian genomic DNA that has been fragmented;
   b) introducing the mixture produced in step (a) into a mammalian cell in vitro; and
   c) propagating said cell under conditions that allow formation of an artificial mammalian chromosome in said cell, wherein said artificial mammalian chromosome comprises a sub-genomic fragment from the DNA fragments of the mixture.

4. A process for preparing an artificial mammalian chromosome comprising:
   a) mixing:
      i) a composition comprising purified DNA fragments comprising telomeric DNA;
      ii) a composition comprising purified DNA fragments comprising centromeric DNA wherein said centromeric DNA is a directional, repetitive array at least 100 kb in length of either alpha-satellite DNA or sequences functionally equivalent to alpha-satellite DNA from other mammals and avians; and
      iii) a composition comprising purified mammalian genomic DNA that has been fragmented; and
   b) introducing the mixture produced in step (a) into a mammalian cell in vitro; and
   c) propagating said cell under conditions that allow the formation of said artificial mammalian chromosome in said cell of the mixture.

* * * * *